(12) United States Patent
Miyauchi et al.

(10) Patent No.: US 8,846,552 B2
(45) Date of Patent: Sep. 30, 2014

(54) SOLUBLE TERMINALLY MODIFIED IMIDE OLIGOMER USING 2-PHENYL-4, 4'-DIAMINODIPHENYL ETHER, VARNISH, CURED PRODUCT THEREOF, IMIDE PREPREG THEREOF, AND FIBER-REINFORCED LAMINATE HAVING EXCELLENT HEAT RESISTANCE

(75) Inventors: Masahiko Miyauchi, Settsu (JP); Yuichi Ishida, Chofu (JP); Toshio Ogasawara, Chofu (JP); Rikio Yokota, Chofu (JP)

(73) Assignees: Kaneka Corporation, Osaka (JP); Japan Aerospace Exporation Agency, Tokyo (JP)

( * ) Notice: Subject to any disclaimer, the term of this patent is extended or adjusted under 35 U.S.C. 154(b) by 750 days.

(21) Appl. No.: 13/062,132

(22) PCT Filed: Sep. 3, 2009

(86) PCT No.: PCT/JP2009/065423
§ 371 (c)(1),
(2), (4) Date: Mar. 3, 2011

(87) PCT Pub. No.: WO2010/027020
PCT Pub. Date: Mar. 11, 2010

(65) Prior Publication Data
US 2011/0165809 A1    Jul. 7, 2011

(30) Foreign Application Priority Data

Sep. 3, 2008 (JP) ................................. 2008-225838
Oct. 22, 2008 (JP) ................................. 2008-271903

(51) Int. Cl.
| | | |
|---|---|---|
| B32B 5/26 | (2006.01) | |
| B05D 3/10 | (2006.01) | |
| C08G 73/10 | (2006.01) | |
| C08K 5/3415 | (2006.01) | |
| C09D 179/08 | (2006.01) | |
| C09J 5/02 | (2006.01) | |
| D04H 3/14 | (2012.01) | |
| D04H 3/16 | (2006.01) | |
| C07D 209/48 | (2006.01) | |
| C08L 79/08 | (2006.01) | |
| C08F 290/06 | (2006.01) | |
| C07D 487/04 | (2006.01) | |
| C08F 299/00 | (2006.01) | |
| C08F 299/02 | (2006.01) | |
| C08J 5/24 | (2006.01) | |
| C08K 7/02 | (2006.01) | |

(52) U.S. Cl.
CPC ........ C08F 290/065 (2013.01); C08G 73/1071 (2013.01); C08J 2379/08 (2013.01); C08K 7/02 (2013.01); C07D 209/48 (2013.01); C08L 79/08 (2013.01); C08G 73/105 (2013.01); C08G 73/1042 (2013.01); C09D 179/08 (2013.01); C07D 487/04 (2013.01); C08F 299/00 (2013.01); C08F 299/02 (2013.01); C08J 5/24 (2013.01)
USPC ..................... 442/136; 428/297.4; 428/300.7; 524/104; 525/426

(58) Field of Classification Search
None
See application file for complete search history.

(56) References Cited

U.S. PATENT DOCUMENTS

| | | | |
|---|---|---|---|
| 5,478,913 A | 12/1995 | Boyce et al. | |
| 5,708,128 A * | 1/1998 | Oikawa et al. | ................ 528/353 |
| 6,281,323 B1 | 8/2001 | Yokota et al. | |
| 6,359,107 B1 | 3/2002 | Connell et al. | |
| 2005/0014925 A1 | 1/2005 | Yokota et al. | |

FOREIGN PATENT DOCUMENTS

| | | |
|---|---|---|
| JP | 9-507510 A | 7/1997 |
| JP | 2000-219741 A | 8/2000 |
| JP | 2003-526704 A | 9/2003 |
| JP | 2004-331801 A | 11/2004 |
| JP | 2005-089766 A | 4/2005 |
| JP | 2006-312699 A | 11/2006 |
| JP | 2006-312700 A | 11/2006 |
| JP | 2007-099969 A | 4/2007 |
| WO | 00/69948 A1 | 11/2000 |

OTHER PUBLICATIONS

International Search Report of PCT/JP2009/065423, date of mailing Nov. 2, 2009.

* cited by examiner

Primary Examiner — Jennifer Chriss
Assistant Examiner — Brett A Crouse
(74) Attorney, Agent, or Firm — Westerman, Hattori, Daniels & Adrian, LLP

(57) ABSTRACT

A novel terminally modified imide oligomer having excellent solubility in organic solvents, excellent solution storage stability, and excellent molding properties such as low melt viscosity. Also, a varnish obtained by dissolving the terminally modified imide oligomer in an organic solvent; a cure product obtained by using the terminally modified imide oligomer and having excellent thermal and mechanical characteristics such as heat resistance, elastic modulus, tensile strength at break and tensile elongation at break; a prepreg; and a fiber-reinforced laminate. The soluble terminally modified imide oligomer is represented by general formula (1). In the formula, $R_1$ and $R_2$ each represents a divalent aromatic diamine residue; $R_3$ and $R_4$ each represents a tetravalent aromatic tetracarboxylic acid residue; $R_5$ and $R_6$ each represents a hydrogen atom or a phenyl group, with $R_5$ or $R_6$ being a phenyl group; m and n satisfy the following relations: $m \geq 1$, $n \geq 0$, $1 \leq m+n \leq 20$ and $0.05 \leq m/(m+n) \leq 1$; and the repeating units may be arranged in blocks or randomly.

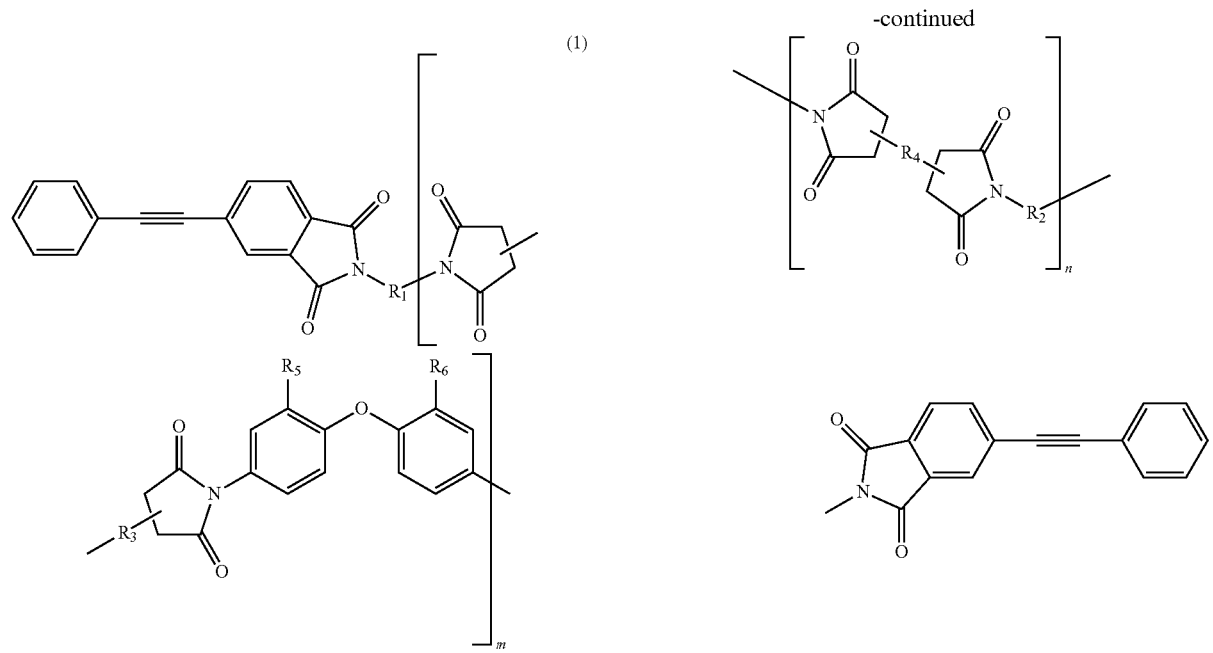
19 Claims, No Drawings

SOLUBLE TERMINALLY MODIFIED IMIDE OLIGOMER USING 2-PHENYL-4, 4'-DIAMINODIPHENYL ETHER, VARNISH, CURED PRODUCT THEREOF, IMIDE PREPREG THEREOF, AND FIBER-REINFORCED LAMINATE HAVING EXCELLENT HEAT RESISTANCE

TECHNICAL FIELD

The present invention relates to a terminally modified imide oligomer, a varnish, and a cured product thereof, in particular to a material for parts usable in a variety of fields that demand favorable moldability and high heat resistance such as parts for aircrafts and devices for the airspace industry.

BACKGROUND ART

Aromatic polyimides, which show heat resistance at the level highest among polymers and are also superior in mechanical and electrical properties, have been used as raw materials in a wide range of applications.

On the other hand, aromatic polyimides are generally poor in processability and not suitable for melt molding or for use as a matrix resin for fiber-reinforced composite materials. For that reason, imide oligomers modified with a thermally crosslinkable group at the terminals were proposed. In particular, imide oligomers modified with 4-(2-phenylethynyl) phthalic anhydride at the terminals are seemingly superior in the balance of moldability, heat resistance, and mechanical properties, and such imide oligomers are described, for example, in Patent Documents 1, 2, and 3 and Nonpatent Literatures 1 and 2. For the purpose of providing a terminally modified imide oligomer giving a cured product superior in heat resistance and mechanical properties and thus superior in usefulness and the cured product thereof, the Patent Document 1 discloses a terminally modified imide oligomer having a logarithmic viscosity of 0.05 to 1 prepared in reaction of 2,3,3',4-biphenyltetracarboxylic dianhydride having a bent and non-planar structure, an aromatic diamine compound, and 4-(2-phenylethynyl)phthalic anhydride and a cured product thereof. It also describes that it is possible, as its advantageous effects of the invention, to obtain a new terminally modified imide oligomer higher in usefulness and also to obtain a cured product of the new terminally modified polyimide superior in heat resistance and mechanical properties such as modulus, tensile strength, and elongation.

However, these terminally modified imide oligomers are only soluble at a concentration of 20 wt % or less in organic solvents such as N-methyl-2-pyrrolidone (hereinafter, referred to simply as NMP) at room temperature (the room temperature means a temperature of 23° C.±2° C. in the present description), and there is observed a phenomenon that the varnish thereof gels within several days, when left still, and thus, such imide oligomers had a problem that it was difficult to store the varnish at higher concentration, as stabilized for an extended period of time.

As described for example in Patent Documents 3 and 4, a method of copolymerizing an acid anhydride monomer having a further bent and non-planar structure, such as 2,2,3',3'-biphenyltetracarboxylic dianhydride, is used as a means of raising the solubility, but it generally leads to decrease in breaking elongation of the resulting polymer, making it brittler.

As described in Patent Documents 4 and 5, a method of copolymerizing a diamine monomer having a sterically bulky structure such as 9,9-bis(4-(4-aminophenoxy)phenyl)fluorene can also be used, but it also generally leads to decrease of the glass transition temperature and the breaking elongation of the resulting polymer, making it brittler.

As described in Patent Document 5, for example in the case of an imide oligomer for injection or transfer molding, the polymerization degree is lowered or the structure of the diamine used is made more flexible, to make the imide oligomer more flowable, but such a treatment only leads to significant drop of the glass transition temperature of the terminal cured product, although it makes the imide oligomer more soluble.

CITATION LIST

Patent Literature

Patent Document 1: JP-A No. 2000-219741
Patent Document 2: JP-A No. 2004-331801
Patent Document 3: JP-A No. 2006-312699
Patent Document 4: JP-A No. 2007-99969
Patent Document 5: JP-A No. 2003-526704

Nonpatent Literature

Nonpatent Literature 1: P. M. Hergenrother and J. G. Smith Jr., Polymer, 35, 4857 (1994).
Nonpatent Literature 2: R. Yokota, S. Yamamoto, S. Yano, T. Sawaguchi, M. Hasegawa, H. Yamaguchi, H. Ozawa and R. Sato, High Perform. Polym., 13, S61 (2001).

SUMMARY OF INVENTION

Technical Problem

Objects of the present invention are to provide a new terminally modified imide oligomer superior in solubility in organic solvent, solution storage stability, and moldability such as low melt viscosity, a varnish prepared by dissolving it in an organic solvent; and a cured product, a prepreg, and a fiber-reinforced laminate prepared by using the terminally modified imide oligomer, which are superior in thermal and mechanical properties such as heat resistance, modulus, tensile breaking strength, and tensile breaking elongation.

Solution to Problem

To solve the problems above, the inventors focused on aromatic polyimide oligomers prepared by using 3,3',4,4'-biphenyltetracarboxylic acid, 1,2,4,5-benzenetetracarboxylic acid or bis(3,4-carboxyphenyl)ether. The inventors considered that, in particular, aromatic polyimide oligomers prepared by using 1,2,4,5-benzenetetracarboxylic acid would give a high-heat resistance and high-strength film and cured product, because of strong intermolecular interaction caused by the rigid and planar structure of pyromellitic imide. However on the other hand, since the imide oligomer is often less flowable, less fusible and less soluble in solvent, because of strong interaction between pyromellitic imide groups, there is currently no report of a terminally modified imide oligomer that can be molded into a cured product having a glass transition temperature of 270° C. or higher and having favorable solvent solubility. The inventors have found that it is possible to prepared a terminally modified imide oligomer sufficiently higher in melt flowability, by using an aromatic diamine containing 2-phenyl-4,4'-diaminodiphenylether, even when 1,2,4,5 benzenetetracarboxylic acid is used, and that the cured product thereof has sufficiently high mechanical strength.

The present invention provides, as new terminally modified imide oligomer, a soluble terminally modified imide oligomer prepared by using 2-phenyl-4,4'-diaminodiphenylether represented by General Formula (1):

[Formula 1]

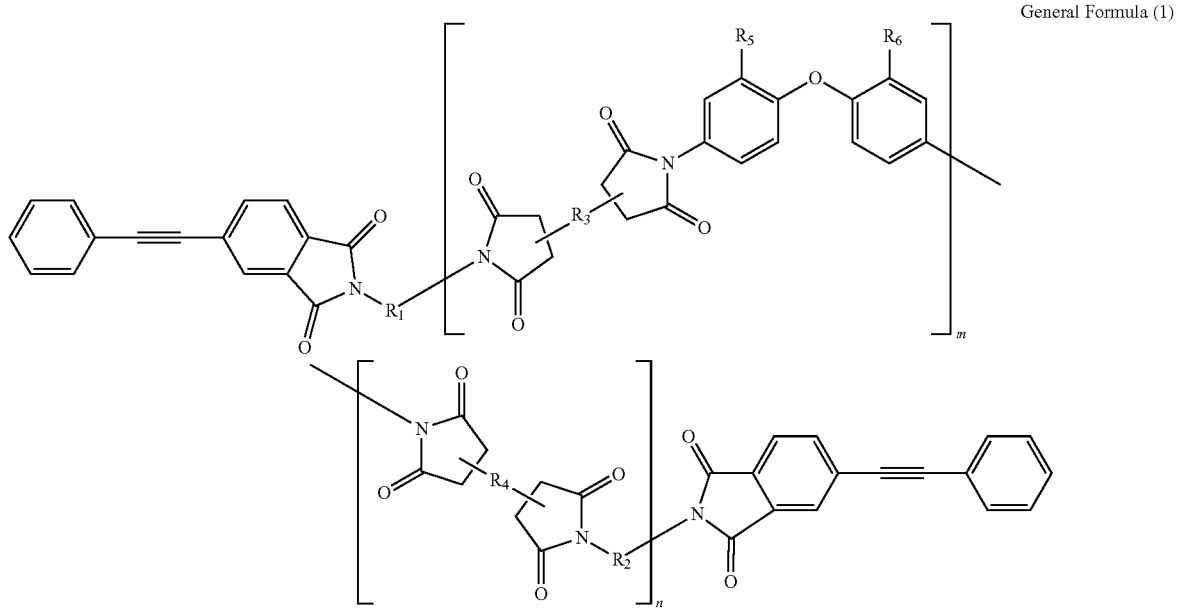

General Formula (1)

(wherein, $R_1$ and $R_2$ each represent bivalent aromatic diamine residue; $R_3$ and $R_4$ each represent tetravalent aromatic tetracarboxylic acid residue; $R_5$ and $R_6$ each represent hydrogen atom or a phenyl group, and either $R_5$ or $R_6$ being a phenyl group; m and n satisfy the following relations: $m \geq 1$, $n \geq 0$, $1 \leq m+n \leq 20$, and $0.05 \leq m/(m+n) \leq 1$; and the repeating units may be arranged in blocks or randomly.)

The aromatic diamine residue in General Formula (1) above is an aromatic organic group present between the two amino groups in the aromatic diamine. The aromatic tetracarboxylic acid residue in General Formula (1) above is an aromatic organic group present as surrounded by 4 carbonyl groups of the aromatic tetracarboxylic acid. The aromatic organic group is an aromatic ring-containing organic group. The aromatic organic group is preferably an organic group having 4 to 30 carbon atoms, more preferably an organic group having 4 to 18 carbon atoms, still more preferably an organic group having 4 to 12 carbon atoms. In addition, the aromatic organic group is preferably a hydrocarbon group having 6 to 30 carbon atoms, more preferably a hydrocarbon group having 6 to 18 carbon atoms, and still more preferably a hydrocarbon group having 6 to 12 carbon atoms.

The aromatic tetracarboxylic acid is preferably 1,2,4,5-benzenetetracarboxylic acid, 3,3',4,4'-biphenyltetracarboxylic acid, bis(3,4-carboxyphenyl)ether, or a combination of at least two of them, and in particular, it is more preferably 1,2,4,5-benzenetetracarboxylic dianhydride, 3,3',4,4'-biphenyltetracarboxylic dianhydride or bis(3,4-carboxyphenyl)ether dianhydride. When the aromatic tetracarboxylic acid is 1,2,4,5-benzenetetracarboxylic acid or 3,3',4,4'-biphenyltetracarboxylic acid, the oligomer is represented by the following General Formula (1-2) or (1-3).

[Formula 2]

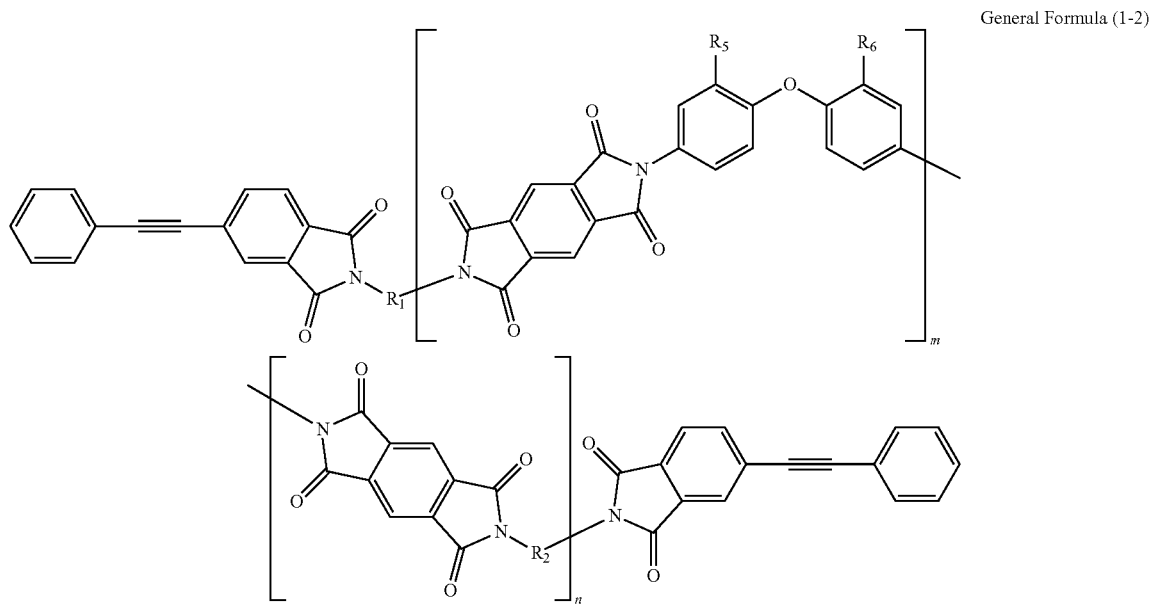

General Formula (1-2)

(wherein, $R_1$ and $R_2$ each represent bivalent aromatic diamine residue; $R_5$ and $R_6$ each represent hydrogen atom or a phenyl group, and either $R_5$ or $R_6$ being a phenyl group; m and n satisfy the following relations: m≥1, n≥0, 1≤m+n≤20, and 0.05≤m/(m+n)≤1; and the repeating units may be arranged in blocks or randomly.)

[Formula 3]

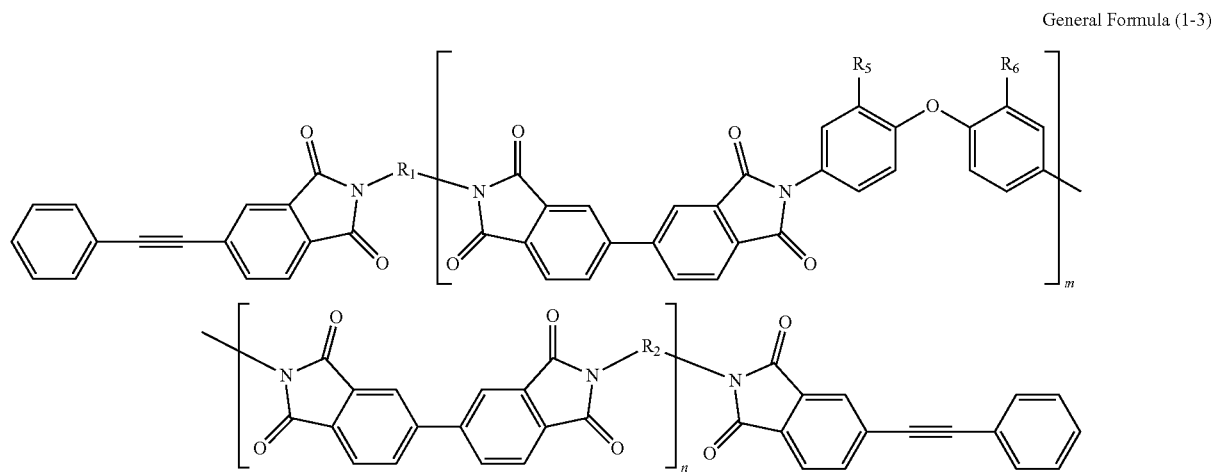

General Formula (1-3)

(wherein, $R_1$ and $R_2$ each represent bivalent aromatic diamine residue; $R_5$ and $R_6$ each represent hydrogen atom or a phenyl group, and either $R_5$ or $R_6$ being a phenyl group; m and n satisfy the following relations: m≥1, n≥0, 1≤m+n≤20, and 0.05≤m/(m+n)≤1; and the repeating units may be arranged in blocks or randomly.)

The terminally modified imide oligomer is preferably a terminally modified imide oligomer soluble in N-methyl-2-pyrrolidone at a solid matter concentration of 30 wt % or more at room temperature.

The present invention also provides a varnish prepared by dissolving the terminally modified imide oligomer in an organic solvent.

The present invention also provides a cured product prepared by curing the terminally modified imide oligomer or the varnish under heat. The cured product preferably has a glass transition temperature (Tg) of 300° C. or higher.

The present invention also provides a film prepared from the cured product, having a tensile breaking elongation of 10% or more.

The present invention also provides an imide prepreg, prepared by impregnating a fiber with the terminally modified imide oligomer or the varnish and drying the fiber.

The present invention also provides a fiber-reinforced laminate plate produced from the terminally modified imide oligomer or the varnish, or an imide prepreg obtained by using same.

Advantageous Effects of Invention

The present invention provides a new terminally modified imide oligomer superior in solubility in organic solvent, solution storage stability, and moldability such as low melt viscosity, which gives a cured product superior in heat resistance and mechanical properties such as tensile modulus, tensile breaking strength, and tensile breaking elongation, and also a varnish containing the same and a cured product thereof. The imide oligomer varnish is significantly superior in hydrolysis resistance, compared to amide acid oligomer varnishes and permits storage, for example without deterioration in viscosity, reliably for an extended period of time. It is also possible to obtain an imide prepreg superior in moldability, strength and reliability, that can be produced under milder molding condition, because there is no concern about generation of water by imidation and thus generation of large pores in the laminate during curing under heat, by coating or impregnating a fiber with the imide oligomer and imide oligomer varnish and drying the resulting fiber, and also to obtain a laminate characteristic of very high heat resistance by using the imide prepreg.

DESCRIPTION OF EMBODIMENTS

The soluble terminally modified imide oligomer according to the present invention represented by General Formula (1) that is prepared by using 2-phenyl-4,4-diaminodiphenylether is preferably one of the followings:

[Formula 4]

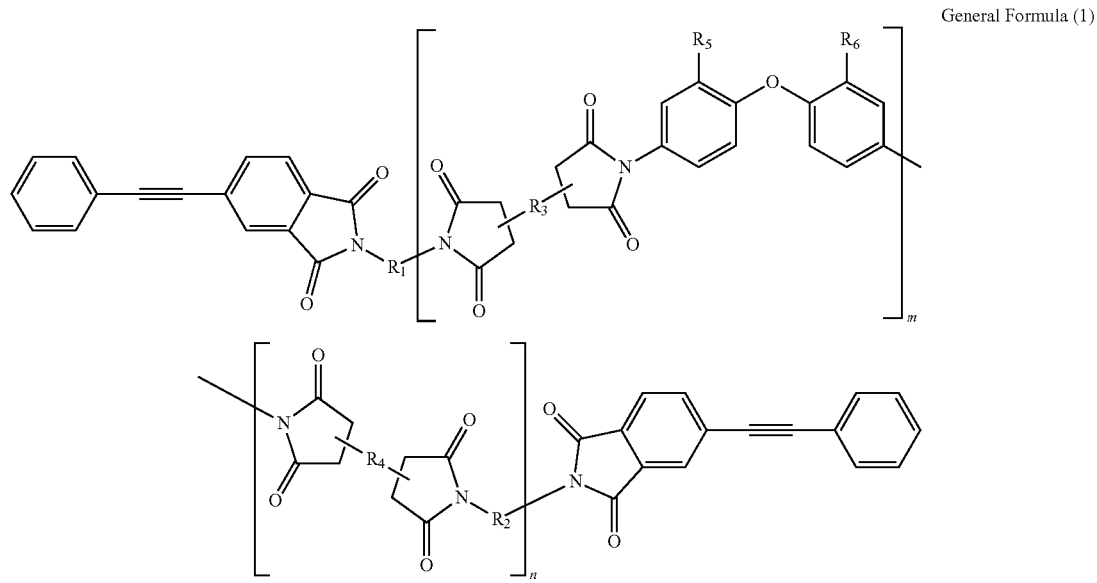

General Formula (1)

(wherein, $R_1$ and $R_2$ each represent bivalent aromatic diamine residue; $R_3$ and $R_4$ each represent tetravalent aromatic tetracarboxylic acid residue; $R_5$ and $R_6$ each represent hydrogen atom or a phenyl group, and either $R_5$ or $R_6$ being a phenyl group; m and n satisfy the following relations: $m \geq 1$, $n \geq 0$, $1 \leq m+n \leq 20$ and $0.05 \leq m/(m+n) \leq 1$; and the repeating units may be arranged in blocks or randomly)

It is specifically an imide oligomer obtained in reaction of one or more tetracarboxylic acids selected from the group consisting 1,2,4,5-benzenetetracarboxylic acid (in particular, its acid dianhydride), 3,3',4,4'-biphenyltetracarboxylic acid (in particular, its acid dianhydride), and bis(3,4-carboxyphenyl)ether (in particular, its acid dianhydride), aromatic diamines including 2-phenyl-4,4'-diaminodiphenylether, and 4-(2-phenylethynyl)phthalic anhydride (hereinafter, referred to simply as PEPA) for introduction of an unsaturated end-group into imide oligomer each in amounts at which the total amount of dicarboxylic acid groups and the total amount of the primary amino groups are almost the same in the presence or absence of organic solvent. (In the case of neighboring dicarboxylic acid groups, it is assumed that there is one mole of acid anhydride group per two moles of carboxyl group.)

Thus in the Formula above, $R_3$ and $R_4$ are each independently selected from the groups derived from the various tetracarboxylic acids above and may be the same as or different from each other. When $m>1$ and $n>1$ are satisfied, the groups $R_3$ ($R_4$) may be the same as or different from each other. $R_5$ and $R_6$ each represent hydrogen atom or a phenyl group, and either $R_5$ or $R_6$ being a phenyl group; when $m>1$ is satisfied, the units where $R_5$ is a phenyl group and $R_6$ a hydrogen atom and the units where $R_5$ is a hydrogen atom and $R_6$ a phenyl group may be present at any ratio.

It is preferably an imide oligomer having imide bonds in the main chain and one or two addition polymerizable unsaturated end-groups derived from 4-(2-phenylethynyl)phthalic anhydride at one or two terminals (favorably two terminals) that satisfies the relationship of $1 \leq m+n \leq 20$ and is solid (powdery) at normal temperature (23° C.).

The 1,2,4,5-benzenetetracarboxylic acid is 1,2,4,5-benzenetetracarboxylic acid, 1,2,4,5-benzenetetracarboxylic acid dianhydride (PMDA) or an acid derivative thereof such as 1,2,4,5-benzenetetracarboxylic ester or salt, and in particular, 1,2,4,5-benzenetetracarboxylic dianhydride is most favorable. The imide oligomer, when $R_3$ and $R_4$ are 1,2,4,5-benzenetetracarboxylic acid, is represented by General Formula (1-2) above.

The 3,3',4,4'-biphenyltetracarboxylic acid is 3,3',4,4'-biphenyltetracarboxylic acid, 3,3',4,4'-biphenyltetracarboxylic dianhydride (s-BPDA) or an acid derivative thereof such as 3,3',4,4'-biphenyltetracarboxylic ester or salt, and in particular, 3,3',4,4'-biphenyltetracarboxylic dianhydride is most favorable. The imide oligomer, when $R_3$ and $R_4$ are 3,3',4,4'-biphenyltetracarboxylic acid, is represented by General Formula (1-3) above.

The bis(3,4-carboxyphenyl)ether above is bis(3,4-carboxyphenyl)ether, bis(3,4-carboxyphenyl)ether dianhydride (s-ODPA) or an acid derivative thereof such as bis(3,4-carboxyphenyl)ether ester or salt, and in particular, bis(3,4-carboxyphenyl)ether dianhydride is most favorable.

Basically in the present invention, 1,2,4,5-benzenetetracarboxylic acid, 3,3',4,4'-biphenyltetracarboxylic acid or bis(3,4-carboxyphenyl)ether is used alone or in combination, but part of 1,2,4,5-benzenetetracarboxylic acid, 3,3',4,4'-biphenyltetracarboxylic acid or bis(3,4-carboxyphenyl)ether may be replaced with another aromatic tetracarboxylic acid compound, if the advantageous effects of the present invention is obtained. It may be replaced, for example, with 3,3',4,4'-benzophenonetetracarboxylic dianhydride (BTDA), 2,3,3',4'-biphenyltetracarboxylic dianhydride (a-BPDA), 2,2',3,3'-biphenyltetracarboxylic dianhydride (i-BPDA), 2,2-bis(3,4-dicarboxyphenyl)methane dianhydride, bis(3,4-carboxyphenyl)ether dianhydride or 1,2,3,4-benzenetetracarboxylic dianhydride, and these tetracarboxylic acid may be used alone or in combination of two or more.

In the present invention, part of the 2-phenyl-4,4'-diaminodiphenylether may be replaced with another aromatic diamine compound, and examples thereof include 1,4-diaminobenzene, 1,3-diaminobenzene, 1,2-diaminobenzene, 2,6-diethyl-1,3-diaminobenzene, 4,6-diethyl-2-methyl-1,3-diaminobenzene, 3,5-diethyltoluene-2,6-diamine, 4,4'-diaminodiphenylether (4,4'-ODA), 3,4'-diaminodiphenylether (3,4'-ODA), 3,3'-diaminodiphenylether, 3,3'-diaminobenzophenone, 4,4'-diaminobenzophenone, 3,3'-diaminodiphenylmethane, 4,4'-diaminodiphenylmethane, bis(2,6-diethyl-4-aminophenyl)methane, 4,4'-methylene-bis(2,6-diethylaniline), bis(2-ethyl-6-methyl-4-aminophenyl)methane, 4,4'-methylene-bis(2-ethyl-6-methylaniline), 2,2-bis(3-aminophenyl)propane, 2,2-bis(4-aminophenyl)propane, 1,3-bis(4-aminophenoxy)benzene, 1,3-bis(3-aminophenoxy)benzene, 1,4-bis(4-aminophenoxy)benzene, 1,4-bis(3-aminophenoxy)benzene, benzidine, 3,3'-dimethylbenzidine, 2,2-bis(4-aminophenoxy)propane, 2,2-bis(3-aminophenoxy)propane, 2,2-bis[4'-(4''-aminophenoxy)phenyl]hexafluoropropane, 9,9-bis(4-aminophenyl)fluorene, 9,9-bis(4-(4-aminophenoxy)phenyl)fluorene and the like, and these compounds may be used alone or in combination of two or more. In particular, the aromatic diamine compound is most preferably 9,9-bis(4-aminophenyl)fluorene, 9,9-bis(4-(4-aminophenoxy)phenyl)fluorene or 1,3-diaminobenzene.

The diamine above is preferably copolymerized for applications demanding higher mechanical strength, and the amount of the copolymeric diamine is preferably 0 to 50 mol %, more preferably 0 to 25 mol %, and still more preferably 0 to 10 mol %, with respect to the total amount of diamines. Specifically in General Formula (1) above, $0.50 \leq m/(m+n) < 1$ is preferable for applications demanding higher mechanical strength, and more preferably $0.75 \leq m/(m+n) < 1$, still more preferably $0.90 \leq m/(m+n) < 1$ and most preferably $0.90 \leq m/(m+n) \leq 0.95$. The diamine for copolymerization is particularly preferably 9,9-bis(4-aminophenyl)fluorene, 9,9-bis(4-(4-aminophenoxy)phenyl)fluorene or 1,3-diaminobenzene. Advantageously, the imide oligomer thus obtained is superior in solubility and also in mechanical properties. Of course in the present invention, a diamine may be used without copolymerization according to applications.

In the present invention, the unsaturated acid anhydride used for terminally modification (end capping) is preferably 4-(2-phenylethynyl)phthalic anhydride. The 4-(2-phenylethynyl)phthalic anhydride is preferably used in an amount in the range of 5 to 200 mol %, particularly 5 to 150 mol % with respect to the total amount of acids.

Hereinafter, the method of producing the terminally modified imide oligomer according to the present invention will be described.

The terminally modified imide oligomer according to the present invention (i.e., terminally 4-(2-phenylethynyl)phthalic anhydride group-containing imide oligomer) is prepared, for example, by preparing an "amide-acid bond-containing oligomer" by polymerizing one or more aromatic tetracarboxylic acid compounds selected from the group consisting of 3,3',4,4'-biphenyltetracarboxylic acid (in particular, its acid dianhydride), 1,2,4,5-benzenetetracarboxylic acid (in particular, the acid dianhydride), and bis(3,4-carboxyphenyl) ether (in particular, its dianhydride), aromatic diamines including 2-phenyl-4,4'-diaminodiphenylether, and (2-phenylethynyl)phthalic anhydride each in amounts, at which the total amount of acid anhydrous groups in all components (in the case of neighboring dicarboxylic acid groups, it is assumed that there is one mole of acid anhydride group per two moles of carboxyl group) and the total amount of amino groups are almost the same, in an organic solvent described below at a reaction temperature of approximately 100° C. or lower, particularly at 80° C. or lower; and dehydrating and thus cyclizing the amide acid oligomer (also called amic acid oligomer) by a method of adding a imidating agent at a low temperature of approximately 0 to 140° C. or by heating the mixture at a high temperature of 140 to 275° C.

A particularly favorable production method for the terminally modified imide oligomer according to the present invention is as follows: First, aromatic diamines including 2-phenyl-4,4'-diaminodiphenylether are dissolved in an organic solvent described below; aromatic tetracarboxylic dianhydrides containing 3,3',4,4'-biphenyltetracarboxylic dianhydride, 1,2,4,5-benzenetetracarboxylic dianhydride, or bis(3,4-carboxyphenyl)ether are added to and dissolved uniformly in the solution, and the mixture is stirred at a reaction temperature of approximately 5 to 60° C. for about 1 to 180 minutes; 4-(2-phenylethynyl)phthalic anhydride is added to and dissolved in the reaction solution, and the mixture is stirred for reaction at a reaction temperature of approximately 5 to 60° C. for about 1 to 180 minutes, to give a terminally modified amide acid oligomer. Subsequently, the reaction solution is stirred at 140 to 275° C. for 5 minutes to 24 hours for imidation of the amide acid oligomer to give a terminally modified imide oligomer, and the reaction solution is cooled to a temperature close to room temperature, as needed, to give the terminally modified imide oligomer according to the present invention. In the reaction above, all or part of the reaction steps are preferably carried out under an inert gas atmosphere such as of nitrogen gas or argon gas or under vacuum.

Examples of the organic solvents for use include N-methyl-2-pyrrolidone (NMP), N,N-dimethylacetamide (DMAc), N,N-diethylacetamide, N-methylcaprolactam, γ-butyrolactone (GBL), cyclohexanone and the like. These solvents may be used alone or in combination of two or more. In selecting these solvents, reference can be made to known technology relevant to soluble polyimides.

The terminally modified imide oligomer thus prepared can be isolated as a powdery product, after the reaction solution is poured for example into water, as needed. The imide oligomer may be used as a powder or, as needed, as a solution, as it is dissolved in a solvent. In addition, the reaction solution may be used, directly as it is or after it is diluted or concentrated, as needed, as a liquid composition (varnish) containing the terminally modified imide oligomer.

The imide oligomer varnish, which is hardly vulnerable to hydrolysis, can be stored for an extended period of time, for example without deterioration in viscosity, compared to amide acid oligomer varnishes. For prevention of gelling, the solvent used for storage for an extended period of time is preferably an amide solvent such as N-methyl-2-pyrrolidone, which is a better solvent.

The terminally modified oligomers according to the present invention different in molecular weight may be used, as they are mixed. Alternatively, the terminally modified imide oligomer according to the present invention may be used, as it is mixed with another soluble polyimide.

The soluble terminally modified imide oligomer according to the present invention represented by General Formula (1) prepared by using 2-phenyl-4,4'-diaminodiphenylether is preferably soluble in the organic solvent, particularly in NMP, at a solid matter concentration of 30 wt % or more at room temperature.

The cured product of the terminally modified imide oligomer according to the present invention in the film shape can be prepared, for example, by applying the terminally modified imide oligomer varnish on a support and curing the wet support under heat at 280 to 500° C. for 5 to 200 minutes. The tensile breaking elongation of the film is preferably 10% or more. The test method will be described below.

The cured product of the terminally modified imide oligomer according to the present invention can be prepared by preparing an intermediate molding by filling the terminally modified imide oligomer powder in a mold such as metal mold and compression-molding the powder at 10 to 280° C. and 1 to 10 kg/cm$^2$ for about 1 second to 100 minutes, and curing the intermediate molding at 280 to 500° C. for about 10 minutes to 40 hours. The glass transition temperature (Tg) of the cured product is preferably 300° C. or higher. The test method will be described below.

The imide prepreg according to the present invention can be prepared, for example, in the following manner.

A liquid composition (varnish) of the terminally modified imide oligomer is prepared by dissolving a powdery terminally modified imide oligomer in an organic solvent or by using the reaction solution as it is or after it is concentrated or diluted. A fiber or a fiber fabric unidirectionally oriented in a flat-plate shape is impregnated with the terminally modified imide oligomer varnish previously adjusted to a favorable concentration and cured in a drier at 20 to 180° C. for 1 minute to 20 hours to give a prepreg. The amount of the resin deposited on the fiber or fiber fabric then is approximately 30 to 50 wt %. The fiber or fiber fabric for use in the invention is not particularly limited, and examples thereof include carbon fiber or its fabric and the like, for use for example in aircrafts.

The fiber-reinforced laminate according to the present invention can be prepared, for example, in the following manner.

It is possible to obtain a laminated sheet by piling a predetermined number of the prepregs and curing the composite under heat at a temperature of 280 to 500° C. and a pressure of 1 to 1000 kg/cm$^2$ for about 10 minutes to 40 hours, for example by using an autoclave or hot press. In addition to the use of prepregs above, it is also possible in the present invention to obtain a laminate sheet by piling fabrics carrying the powder of the terminally modified imide oligomer according to the present invention thereon and curing the pile under heat similarly to above.

The fiber-reinforced laminate according to the present invention thus obtained preferably has a glass transition temperature (Tg) of 300° C. or higher. The test method will be described below.

EXAMPLES

Hereinafter, the present invention will be described with reference to some Examples, but it should be understood that the present invention is not restricted by these Examples. Measuring conditions for various properties are as follows:

<Test Methods>

(1) Measurement of 5% weight-loss temperature: measured by using SDT-2960 type thermogravimetric analyzer (TGA) manufactured by TA Instruments under nitrogen stream at a heating speed of 5° C./min.

(2) Measurement of the glass transition temperature of cured product: measured by using DSC-2010 type differential scanning calorimeter (DSC) manufactured by TA Instruments under nitrogen stream at a heating speed of 5° C./min.

(3) Measurement of the glass transition temperature of fiber-reinforced laminate: measured by using DMA-Q-800 type dynamic mechanical analyzer (DMA) manufactured by TA Instruments at 0.1% deformation and 1-Hz frequency in the cantilever mode under nitrogen stream at a heating speed of 3° C./min. The point of inflection where the storage modulus starts to decline was used as the glass transition temperature.

(4) Measurement of lowest melt viscosity: measured by using AR2000 type rheometer manufactured by TA Instruments and 25-mm parallel plates at a heating rate of 4° C./min.

(5) Tensile test (measurement of modulus, breaking strength and breaking elongation): measured by using TENSILON/UTM-II-20 manufactured by ORIENTECH. CO., LTD at a tension speed of 3 mm/min at room temperature. The test piece used was a film having a length of 20 mm, a width of 3 mm, and a thickness of 80 to 175 μm.

Example 1

2.761 g (10 mmol) of 2-phenyl-4,4'-diaminodiphenylether and 10 mL of N-methyl-2-pyrrolidone were placed and dissolved in a 100 mL three-necked flask equipped with a thermometer, a stirring bar, and a nitrogen-supplying tube; 2.354 g (8 mmol) of 3,3',4,4'-biphenyltetracarboxylic dianhydride and 2.4 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; the mixture was allowed to react for terminal modification under nitrogen stream at room temperature for 12 hours and then stirred at 195° C. for 5 hours for imidation.

After cooling, the reaction solution was poured into 900 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue, $R_3$ represents a 3,3',4,4'-biphenyltetracarboxylic dianhydride residue; and m=4 and n=0 on average. (More specifically, a structure is represented by General Formula (1-3). Terminally modified imide oligomers were prepared similarly in Examples 2 to 5).

[Formula 5]

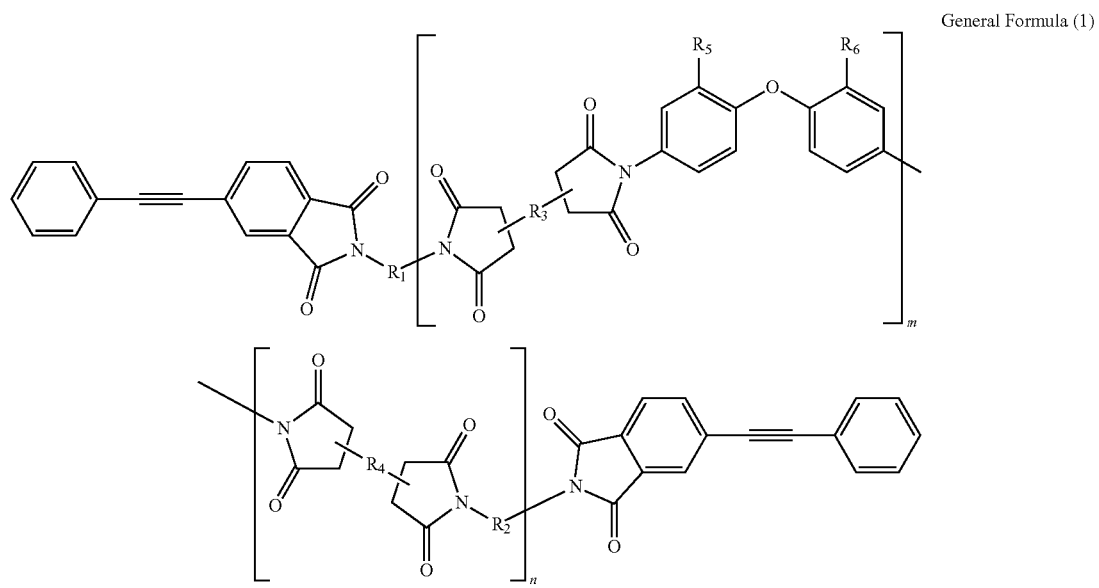

General Formula (1)

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % gelled in several days when left still at room temperature, but returned to liquid state when heated once again to 80° C. The solution gelled again in several days when left still at room temperature. The lowest melt viscosity of the powdery terminally modified imide oligomer was 104 Pa·sec (340° C.) before curing. The film-shaped cured product (thickness; 109 μm) obtained by heating the powdery terminally modified imide oligomer at 370° C. by using a hot press for 1 hour had a Tg of 309° C. (DSC) and a 5% weight-loss temperature of 549° C., as determined by TGA. Analysis of the mechanical properties by tensile tests showed that had a modulus of 3.23 GPa, a breaking strength of 139 MPa, and a breaking elongation of 14%.

Comparative Example 1

2.002 g (10 mmol) of 4,4'-diaminodiphenylether and 16 mL of N-methyl-2-pyrrolidone were placed and dissolved in a 100 mL three-necked flask equipped with a thermometer, a stirring bar, and a nitrogen-supplying tube; 2.354 g (8 mmol) of 3,3',4,4'-biphenyltetracarboxylic dianhydride was added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; the mixture was allowed to react for terminal modification under nitrogen stream at room temperature for 18 hours and then stirred at 175° C. for 5 hours for imidation. The imide oligomer precipitated during the imidation reaction.

After cooling, the reaction solution was poured into 900 mL of ion-exchange water, and the precipitated powder was collected by filtration. The powder was washed with 60 mL of methanol for 30 minutes and filtered, and the powder obtained by filtration was dried under reduced pressure at 130° C. for one day, to give a product. The terminally modified imide oligomer thus obtained has a structure of the following General Formula (2), in which $R_1$ represents a 4,4'-diaminodiphenylether residue; and m=4 and n=0 on average.

[Formula 6]

General Formula (2)

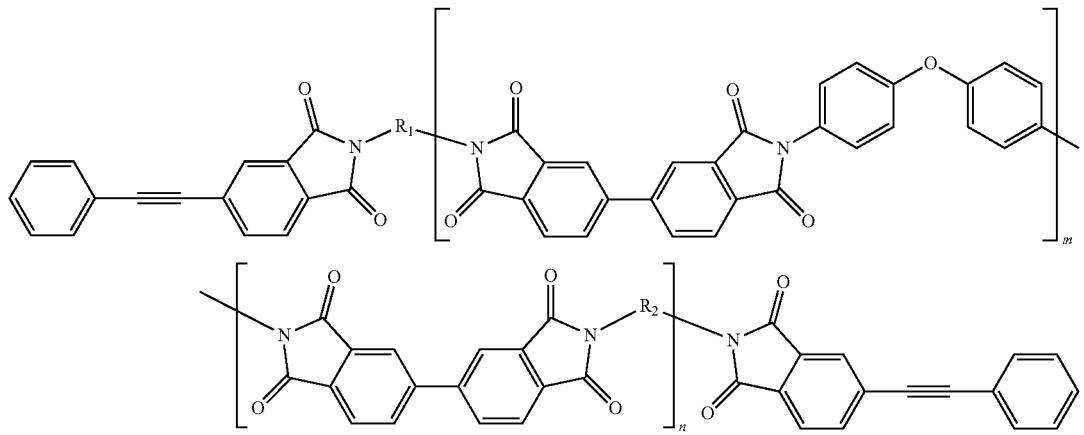

The powdery uncured product of terminally modified imide oligomer thus obtained was insoluble in NMP solvent. The powdery terminally modified imide oligomer did not show melt fluidity even at 300° C. or higher and did not give a favorable shaped product (cured film-shaped product).

Example 2

2.071 g (7.5 mmol) of 2-phenyl-4,4'-diaminodiphenylether, 1.332 g (2.5 mmol) of 9,9-bis(4-(4-aminophenoxy)phenyl)fluorene and 10 mL of N-methyl-2-pyrrolidone were placed and dissolved in a 100 mL three-necked flask equipped with a thermometer, a stirring bar, and a nitrogen-supplying tube; 2.354 g (8 mmol) of 3,3',4,4'-biphenyltetracarboxylic dianhydride and 3.7 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, the reaction solution was poured into 200 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue or a 9,9-bis(4-(4-aminophenoxy)phenyl)fluorene residue; $R_2$ represents a fluorenylidene diphenylether residue; $R_3$ and $R_4$ each represent a 3,3',4,4'-biphenyltetracarboxylic dianhydride residue; and m=3 and n=1 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % gelled in several days when left still at room temperature, but returned to liquid state when heated once again to 80° C. The solution gelled again in several days when left still at room temperature. The lowest melt viscosity of the powdery terminally modified imide oligomer was 251 Pa·sec (352° C.) before curing. The film-shaped cured product (thickness: 105 μm) obtained by heating the powdery terminally modified imide oligomer at 370° C. by using a hot press for 1 hour had a Tg of 317° C. (DSC) and a 5% weight-loss temperature of 549° C., as determined by TGA. Analysis of the mechanical properties by tensile tests showed that had a modulus of 3.35 GPa, a breaking strength of 125 MPa, and a breaking elongation of 10%.

Example 3

1.3807 g (5 mmol) of 2-phenyl-4,4'-diaminodiphenylether, 2.6631 g (5 mmol) of 9,9-bis(4-(4-aminophenoxy)phenyl)fluorene and 10 mL of N-methyl-2-pyrrolidone were placed and dissolved in a 100 mL three-necked flask equipped with a thermometer, a stirring bar, and a nitrogen-supplying tube; 2.354 g (8 mmol) of 3,3',4,4'-biphenyltetracarboxylic dianhydride and 4.6 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, the reaction solution was poured into 200 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue or a 9,9-bis(4-(4-aminophenoxy)phenyl)fluorene residue; $R_2$ represents a 9,9-bis(4-(4-aminophenoxy)phenyl)fluorene residue; and $R_3$ and $R_4$ each represent a 3,3',4,4'-biphenyltetracarboxylic dianhydride residue; and m=2 and n=2 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % gelled in several days when left still at room temperature, but returned to liquid state when heated once again to 80° C. The solution gelled again in several days when left still at room temperature. The lowest melt viscosity of the powdery terminally modified imide oligomer was 398 Pa·sec (354° C.) before curing. The film-shaped cured product (thickness: 98 μm) obtained by heating the powdery terminally modified imide oligomer at 370° C. by using a hot press for 1 hour had a Tg of 317° C. (DSC) and a 5% weight-loss temperature of 561° C., as determined by TGA. Analysis of the mechanical properties by tensile tests showed that had a modulus of 3.31 GPa, a breaking strength of 126 MPa, and a breaking elongation of 18%.

Comparative Example 2

1.001 g (5 mmol) of 4,4'-diaminodiphenylether, 2.6631 g (5 mmol) of 9,9-bis(4-(4-aminophenoxy)phenyl)fluorene and 10 mL of N-methyl-2-pyrrolidone were placed and dissolved in a 100 mL three-necked flask equipped with a thermometer, a stirring bar, and a nitrogen-supplying tube; 2.354 g (8 mmol) of 3,3',4,4'-biphenyltetracarboxylic dianhydride and 4.6 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated during the imidation reaction.

After cooling, the reaction solution was poured into 900 mL of ion-exchange water, and the precipitated powder was collected by filtration. The powder was washed with 60 mL of methanol for 30 minutes and filtered, and the powder obtained by filtration was dried under reduced pressure at 130° C. for one day, to give a product. The terminally modified imide oligomer thus obtained has a structure of the following General Formula (2), in which $R_1$ represents a 4,4'-diaminodiphenylether residue or a 9,9-bis(4-(4-aminophenoxy)phenyl)fluorene residue; $R_2$ represents a 9,9-bis(4-(4-aminophenoxy)phenyl)fluorene residue; and m=2 and n=2 on average.

The powdery uncured product of terminally modified imide oligomer thus obtained was insoluble in NMP solvent at room temperature. The lowest melt viscosity of the powdery terminally modified imide oligomer was 1084 Pa·sec (349° C.) before curing. The film-shaped cured product (thickness: 150 μm) obtained by heating the powdery terminally modified imide oligomer at 370° C. by using a hot press for 1 hour had a Tg of 330° C. (DSC) and a 5% weight-loss temperature of 550° C., as determined by TGA. Analysis of the mechanical properties by tensile tests showed that had a modulus of 2.84 GPa, a breaking strength of 117 MPa, and a breaking elongation of 12%.

Example 4

2.071 g (7.5 mmol) of 2-phenyl-4,4'-diaminodiphenylether, 0.8711 g (2.5 mmol) of 9,9-bis(4-aminophenyl)fluorene and 10 mL of N-methyl-2-pyrrolidone were placed and dissolved in a 100 mL three-necked flask equipped with a thermometer, a stirring bar, and a nitrogen-supplying tube; 2.354 g (8 mmol) of 3,3',4,4'-biphenyltetracarboxylic dianhydride and 1.6 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, the reaction solution was poured into 200 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue or a 9,9-bis(4-aminophenyl)fluorene residue; $R_2$ represents a 9,9-bis(4-aminophenyl)fluorene residue; $R_3$ and $R_4$ each represent a 3,3',4,4'-biphenyltetracarboxylic dianhydride residue; and m=3 and n=1 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % gelled in several days when left still at room temperature, but returned to liquid state when heated once again to 80° C. The solution gelled again in several days when left still at room temperature. The lowest melt viscosity of the powdery terminally modified imide oligomer was 2244 Pa·sec (345° C.) before curing. The film-shaped cured product (thickness: 113 μm) obtained by heating the powdery terminally modified imide oligomer at 370° C. by using a hot press for 1 hour had a Tg of 346° C. (DSC) and a 5% weight-loss temperature of 553° C., as determined by TGA. Analysis of the mechanical properties by tensile tests showed that had a modulus of 3.99 GPa, a breaking strength of 155 MPa, and a breaking elongation of 12%.

Comparative Example 3

1.5018 g (7.5 mmol) of 4,4'-diaminodiphenylether, 0.8711 g (2.5 mmol) of 9,9-bis(4-aminophenyl)fluorene, and 10 mL of N-methyl-2-pyrrolidone were placed and dissolved in a 100 mL three-necked flask equipped with a thermometer, a stirring bar, and a nitrogen-supplying tube; 2.354 g (8 mmol) of 3,3' 4,4 biphenyltetracarboxylic dianhydride and 1.6 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated when the solution was cooled to room temperature after imidation reaction.

After cooling, the reaction solution was poured into 900 mL of ion-exchange water, and the precipitated powder was collected by filtration. The powder was washed with 60 mL of methanol for 30 minutes and filtered, and the powder obtained by filtration was dried under reduced pressure at 130° C. for one day, to give a product. The terminally modified imide oligomer thus obtained has a structure of the following General Formula (2), in which $R_1$ represents a 4,4'-diaminodiphenylether residue or a 9,9-bis(4-aminophenyl)fluorene residue; $R_2$ represents a 9,9-bis(4-aminophenyl)fluorene residue; and m=3 and n=1 on average.

The powdery uncured product of terminally modified imide oligomer thus obtained was insoluble in NMP solvent. The powdery terminally modified imide oligomer did not show melt fluidity even at 300° C. or higher and did not give a favorable shaped product (cured film-shaped product).

Example 5

1.3807 g (5 mmol) of 2-phenyl-4,4'-diaminodiphenylether, 1.7422 g (5 mmol) of 9,9-bis(4-aminophenyl)fluorene and 10 mL of N-methyl-2-pyrrolidone were placed and dissolved in a 100 mL three-necked flask equipped with a thermometer, a stirring bar, and a nitrogen-supplying tube; 2.354 g (8 mmol) of 3,3',4,4'-biphenyltetracarboxylic dianhydride and 3.1 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, the reaction solution was poured into 200 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue or a 9,9-bis(4-aminophenyl)fluorene residue; $R_2$ represents a 9,9-bis(4-aminophenyl)fluorene residue; $R_3$ and $R_4$ each represent a 3,3',4,4'-biphenyltetracarboxylic dianhydride residue; and m=2 and n=2 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % did not gel even after storage for one month. The lowest melt viscosity of the powdery terminally modified imide oligomer was 2765 Pa·sec (344° C.) before curing. The film-shaped cured product (thickness: 156 μm) obtained by heating the powdery terminally modified imide oligomer at 370° C. by using a hot press for 1 hour had a Tg of 366° C. (DSC) and a 5% weight-loss temperature of 552° C., as determined by TGA. Analysis of the mechanical properties by tensile tests showed that had a modulus of 3.47 GPa, a breaking strength of 140 MPa, and a breaking elongation of 10%.

Comparative Example 4)

1.0012 g (5 mmol) of 4,4'-diaminodiphenylether, 1.7422 g (5 mmol) of 9,9-bis(4-aminophenyl)fluorene and 10 mL of N-methyl-2-pyrrolidone were placed and dissolved in a 100 mL three-necked flask equipped with a thermometer, a stirring bar, and a nitrogen-supplying tube; 2.354 g (8 mmol) of 3,3',4,4'-biphenyltetracarboxylic dianhydride and 1.6 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated when the solution was cooled to room temperature after imidation reaction.

After cooling, the reaction solution was poured into 900 mL of ion-exchange water, and the precipitated powder was collected by filtration. The powder was washed with 60 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 4,4'-diaminodiphenylether residue or a 9,9-bis(4-aminophenyl)fluorene residue; $R_2$ represents a 9,9-bis(4-aminophenyl)fluorene residue; and m=2 and n=2 on average.

The powdery uncured product of terminally modified imide oligomer thus obtained was insoluble in NMP solvent at room temperature. The lowest melt viscosity of the powdery terminally modified imide oligomer was 1695 Pa·sec (341° C.) before curing. The film-shaped cured product (thickness: 155 μm) obtained by heating the powdery terminally modified imide oligomer at 370° C. by using a hot press for 1 hour had a Tg of 345° C. (DSC) and a 5% weight-loss temperature of 547° C., as determined by TGA. Analysis of the mechanical properties by tensile tests showed that had a modulus of 2.82 GPa, a breaking strength of 106 MPa, and a breaking elongation of 14%.

Comparative Example 5

3.4844 g (10 mmol) of 9,9-bis(4-aminophenyl)fluorene and 10 mL of N-methyl-2-pyrrolidone were placed and dissolved in a 100 mL three-necked flask equipped with a thermometer, a stirring bar, and a nitrogen-supplying tube; 2.354 g (8 mmol) of 3,3',4,4'-biphenyltetracarboxylic dianhydride and 4.6 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated during the imidation reaction.

After cooling, the reaction solution was poured into 900 mL of ion-exchange water, and the precipitated powder was collected by filtration. The powder was washed with 60 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ and $R_2$ each represent a 9,9-bis(4-aminophenyl)fluorene residue, and m=0 and n=4 on average.

The powdery uncured product of terminally modified imide oligomer thus obtained was insoluble in NMP solvent at room temperature. The powdery terminally modified imide oligomer did not show melt fluidity even at 300° C. or higher and did not give a favorable shaped product (cured film-shaped product).

Example 6

2.7613 g (10 mmol) of 2-phenyl-4,4'-diaminodiphenylether and 10 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride and 0.8 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.9929 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, the reaction solution was poured into 900 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue; $R_3$ represents a 1,2,4,5-benzenetetracarboxylic dianhydride residue; and m=4 and n=0 on average. (More specifically, a structure is represented by General Formula (1-2). Terminally modified imide oligomers were prepared similarly in Examples 7 to 16).

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % gelled in several days when left still at room temperature, but returned to liquid state when heated once again to 80° C. The solution gelled again in several days when left still at room temperature. The lowest melt viscosity of the powdery terminally modified imide oligomer was 208 Pa·s (343° C.) before curing. The film-shaped cured product (thickness: 99 μm) obtained by heating the powdery terminally modified imide oligomer at 370° C. by using a hot press for 1 hour had a Tg of 354° C. (DSC) and a 5% weight-loss temperature of 540° C., as determined by TGA. Analysis of the mechanical properties by tensile tests showed that had a modulus of 3.24 GPa, a breaking strength of 133 MPa, and a breaking elongation of 17%.

Comparative Example 6

2.0024 g (10 mmol) of 4,4'-diaminodiphenylether and 9.3 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride was added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.9929 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated during the imidation reaction.

After cooling, the reaction solution was poured into 900 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the fol-

[Formula 7]

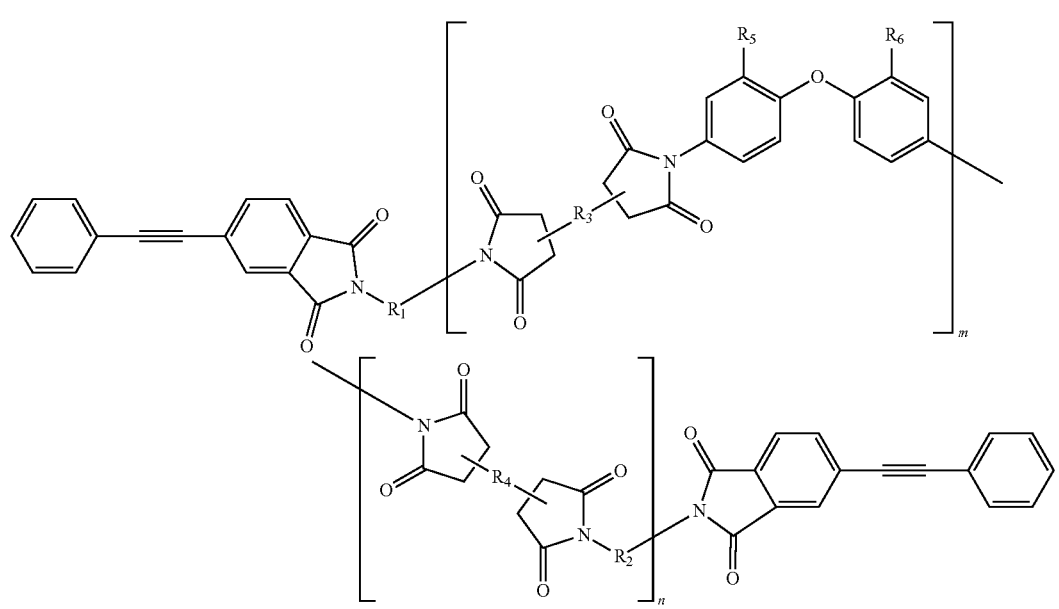

General Formula (1)

lowing General Formula (3), in which $R_1$ represents a 4,4'-diaminodiphenylether residue, and m=4 and n=0 on average.

[Formula 8]

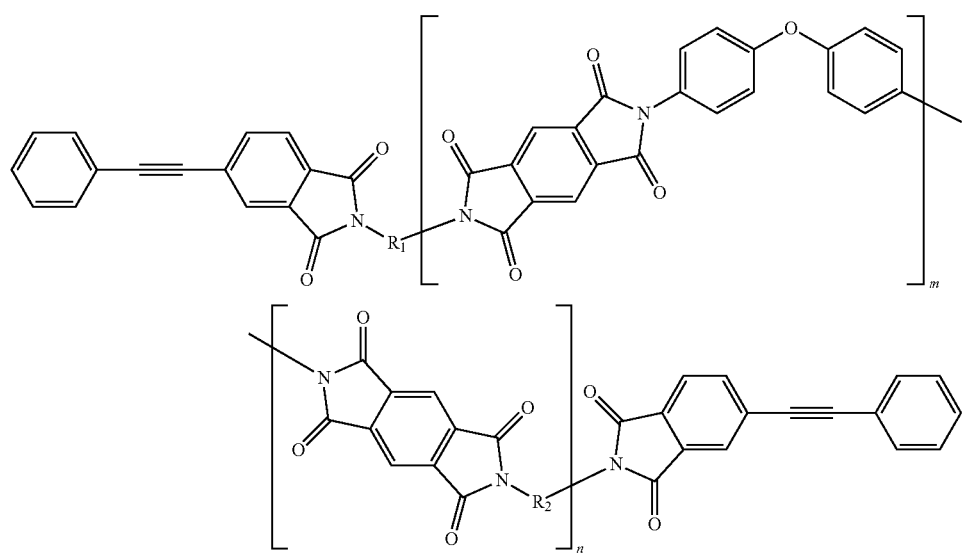

General Formula (3)

The powdery uncured product of terminally modified imide oligomer thus obtained was insoluble in NMP solvent at room temperature. The powdery terminally modified imide oligomer did not show melt fluidity even at 300° C. or higher and did not give a favorable shaped product (cured film-shaped product).

Example 7

2.6232 g (9.5 mmol) of 2-phenyl-4,4'-diaminodiphenylether, 0.2661 g (0.5 mmol) of 9,9-bis(4-(4-aminophenoxy)phenyl)fluorene and 10 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride and 1.1 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.9929 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, the reaction solution was poured into 900 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue or a 9,9-bis(4-(4-aminophenoxy)phenyl)fluorene residue; $R_2$ represents a 9,9-bis(4-(4-aminophenoxy)phenyl)fluorene residue; $R_3$ and $R_4$ each represent a 1,2,4,5-benzenetetracarboxylic dianhydride residue; and m=3.8 and n=0.2 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % did not gel even after storage for one month. The lowest melt viscosity of the powdery terminally modified imide oligomer was 159 Pa·s (341° C.) before curing. The film-shaped cured product (thickness: 115 µm) obtained by heating the powdery terminally modified imide oligomer at 370° C. by using a hot press for 1 hour had a Tg of 352° C. (DSC) and a 5% weight-loss temperature of 536° C., as determined by TGA. Analysis of the mechanical properties by tensile tests showed that had a modulus of 2.87 GPa, a breaking strength of 122 MPa, and a breaking elongation of 21%.

Comparative Example 7

1.9023 g (9.5 mmol) of 4,4'-diaminodiphenylether, 0.2661 g (0.5 mmol) of 9,9-bis(4-(4-aminophenoxy)phenyl)fluorene and 9.7 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride was added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated during the imidation reaction.

After cooling, the reaction solution was poured into 900 mL of ion-exchange water, and the precipitated powder was collected by filtration. The powder was washed with 60 mL of methanol for 30 minutes and filtered, and the powder obtained by filtration was dried under reduced pressure at 130° C. for one day, to give a product. The terminally modified imide oligomer thus obtained has a structure of the following General Formula (3), in which $R_1$ represents a 4,4'-diaminodiphenylether residue or a 9,9-bis(4-(4-aminophenoxy)phenyl)fluorene residue; $R_2$ represents a 9,9-bis(4-(4-aminophenoxy)phenyl)fluorene residue; and m=3.8 and n=0.2 on average.

The powdery uncured product of terminally modified imide oligomer thus obtained was insoluble in NMP solvent at room temperature. The powdery terminally modified imide oligomer did not show melt fluidity even at 300° C. or higher and did not give a favorable shaped product (cured film-shaped product).

Example 8

2.4850 g (9.0 mmol) of 2-phenyl-4,4'-diaminodiphenylether, 0.5326 g (1.0 mmol) of 9,9-bis(4-(4-aminophenoxy)phenyl)fluorene and 10 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride and 1.3 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.9929 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, the reaction solution was poured into 200 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue or a 9,9-bis(4-(4-aminophenoxy)phenyl)fluorene residue; $R_2$ represents a 9,9-bis(4-(4-aminophenoxy)phenyl)fluorene residue; $R_3$ and $R_4$ each represent a 1,2,4,5-benzenetetracarboxylic dianhydride residue; and m=3.6 and n=0.4 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % did not gel even after storage for one month. The lowest melt viscosity of the powdery terminally modified imide oligomer was 76 Pa·s (335° C.) before curing. The film-shaped cured product (thickness: 115 μm) obtained by heating the powdery terminally modified imide oligomer at 370° C. by using a hot press for 1 hour had a Tg of 350° C. (DSC) and a 5% weight-loss temperature of 538° C., as determined by TGA. Analysis of the mechanical properties by tensile tests showed that had a modulus of 2.79 GPa, a breaking strength of 115 MPa, and a breaking elongation of 19%.

Comparative Example 8

1.8022 g (9.0 mmol) of 4,4'-diaminodiphenylether, 0.5326 g (1.0 mmol) of 9,9-bis(4-(4-aminophenoxy)phenyl)fluorene and 10 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride was added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; the mixture was allowed to react for terminal modification under nitrogen stream at room temperature for 12 hours and then stirred at 195° C. for 5 hours for imidation. The imide oligomer precipitated during the imidation reaction.

After cooling, the reaction solution was poured into 900 mL of ion-exchange water, and the precipitated powder was collected by filtration. The powder was washed with 60 mL of methanol for 30 minutes and filtered, and the powder obtained by filtration was dried under reduced pressure at 130° C. for one day, to give a product. The terminally modified imide oligomer thus obtained has a structure of the following General Formula (3), in which $R_1$ represents a 4,4'-diaminodiphenylether residue or a 9,9-bis(4-(4-aminophenoxy)phenyl)fluorene residue; $R_2$ represents a 9,9-bis(4-(4-aminophenoxy)phenyl)fluorene residue; and m=3.6 and n=0.4 on average.

The powdery uncured product of terminally modified imide oligomer thus obtained was insoluble in NMP solvent at room temperature. The powdery terminally modified imide oligomer did not show melt fluidity even at 300° C. or higher and did not give a favorable shaped product (cured film-shaped product).

Example 9

2.0709 g (7.5 mmol) of 2-phenyl-4,4'-diaminodiphenylether, 1.3315 g (2.5 mmol) of 9,9-bis(4-(4-aminophenoxy)phenyl)fluorene and 10 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride and 2.1 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.9929 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, the reaction solution was poured into 200 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue or a 9,9-bis(4-(4-aminophenoxy)phenyl)fluorene residue; $R_2$ represents a 9,9-bis(4-(4-aminophenoxy)phenyl)fluorene residue; $R_3$ and $R_4$ each represent a 1,2,4,5-benzenetetracarboxylic dianhydride residue; and m=3 and n=1 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % did not gel even after storage for 1 month. The lowest melt viscosity of the powdery terminally modified imide oligomer was 553 Pa·s (345° C.) before curing. The film-shaped cured product (thickness: 151 μm) obtained by heating the powdery terminally modified imide oligomer at 370° C. by using a hot press for 1 hour had a Tg of 358° C. (DSC) and a 5% weight-loss temperature of 538° C., as determined by TGA. Analysis of the mechanical properties by tensile tests showed that had a modulus of 2.96 GPa, a breaking strength of 119 MPa, and a breaking elongation of 17%.

Comparative Example 9

1.5018 g (7.5 mmol) of 4,4'-diaminodiphenylether, 1.3315 g (2.5 mmol) of 9,9-bis(4-(4-aminophenoxy)phenyl)fluorene and 10 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride and 4.4 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated during the imidation reaction.

After cooling, the reaction solution was poured into 900 mL of ion-exchange water, and the precipitated powder was collected by filtration. The powder was washed with 60 mL of methanol for 30 minutes and filtered, and the powder obtained by filtration was dried under reduced pressure at 130° C. for one day, to give a product. The terminally modified imide oligomer thus obtained has a structure of the following General Formula (3), in which $R_1$ represents a 4,4'-diaminodiphenylether residue or a 9,9-bis(4-(4-aminophenoxy)phenyl)fluorene residue; $R_2$ represents a 9,9-bis(4-(4-aminophenoxy)phenyl)fluorene residue; and m=3 and n=1 on average.

The powdery uncured product of terminally modified imide oligomer thus obtained was insoluble in NMP solvent at room temperature. The powdery terminally modified imide oligomer did not show melt fluidity even at 300° C. or higher and did not give a favorable shaped product (cured film-shaped product).

Comparative Example 10

5.3261 g (10 mmol) of 9,9-bis(4-(4-aminophenoxy)phenyl)fluorene and 15 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride and 0.9 mL of N-methyl-2-pyrrolidone were added thereto; the mixture was allowed to react in polymerization reaction under nitrogen stream at room temperature for 2.5 hours, at 60° C. for 1.5 hours and additionally at room temperature for 1 hour, to give an amide acid oligomer. 0.9929 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated during the imidation reaction.

After cooling, the reaction solution was poured into 900 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (3), in which $R_1$ and $R_2$ each represent a 9,9-bis(4-(4-aminophenoxy)phenyl)fluorene residue; and m=0 and n=4 on average.

The powdery uncured product of terminally modified imide oligomer thus obtained was insoluble in NMP solvent at room temperature. The powdery terminally modified imide oligomer did not show melt fluidity even at 300° C. or higher and did not give a favorable shaped product (cured film-shaped product).

Example 10

2.6232 g (9.5 mmol) of 2-phenyl-4,4'-diaminodiphenylether, 0.1742 g (0.5 mmol) of 9,9-bis(4-aminophenyl)fluorene and 10 mL of N-methyl-2-pyrrolidone were placed and dissolved in a 100 mL three-necked flask equipped with a thermometer, a stirring bar, and a nitrogen-supplying tube; 1.7450 (8 mmol) of 1,2,4,5-benzenetetracarboxylic dianhydride and 0.9 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, the reaction solution was poured into 900 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue or a 9,9-bis(4-aminophenyl)fluorene residue; $R_2$ represents a 9,9-bis(4-aminophenyl)fluorene residue; $R_3$ and $R_4$ each represent a 1,2,4,5-benzenetetracarboxylic dianhydride residue; and m=3.8 and n=0.2 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % did not gel even after storage for one month. The lowest melt viscosity of the powdery terminally modified imide oligomer was 226 Pa·s (341° C.) before curing. The film-shaped cured product (thickness: 110 μm) obtained by heating the powdery terminally modified imide oligomer at 370° C. by using a hot press for 1 hour had a Tg of 353° C. (DSC) and a 5% weight-loss temperature of 538° C., as determined by TGA. Analysis of the mechanical properties by tensile tests showed that had a modulus of 2.99 GPa, a breaking strength of 122 MPa, and a breaking elongation of 15%.

Comparative Example 11

1.9023 g (9.5 mmol) of 4,4'-diaminodiphenylether, 0.1742 g (0.5 mmol) of 9,9-bis(4-aminophenyl)fluorene and 9.6 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride was added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated during the imidation reaction.

After cooling, the reaction solution was poured into 900 mL of ion-exchange water for 30 minutes and the precipitated powder was collected by filtration. The powder was washed with 60 mL of methanol for 30 minutes and filtered, and the powder obtained by filtration was dried under reduced pressure at 130° C. for one day, to give a product. The terminally modified imide oligomer thus obtained has a structure of the following General Formula (3), in which $R_1$ represents a 4,4'-diaminodiphenylether residue or a 9,9-bis(4-aminophenyl)fluorene residue; $R_2$ represents a 9,9-bis(4-aminophenyl)fluorene residue; and m=3.8 and n=0.2 on average.

The powdery uncured product of terminally modified imide oligomer thus obtained was insoluble in NMP solvent at room temperature. The powdery terminally modified imide oligomer did not show melt fluidity even at 300° C. or higher and did not give a favorable shaped product (cured film-shaped product).

Example 11

220.79 g (0.80 mol) of 2-phenyl-4,4'-diaminodiphenylether, 30.95 g (0.089 mol) of 9,9-bis(4-aminophenyl)fluorene and 860 mL of N-methyl-2-pyrrolidone were placed and dissolved in a 2000 mL three-necked flask equipped with a thermometer, a stirring bar, and a nitrogen-supplying tube; 155.04 g (0.711 mol) of 1,2,4,5-benzenetetracarboxylic dianhydride and 33 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 88.22 g (0.355 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, part of the reaction solution was poured into 500 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue or a 9,9-bis(4-aminophenyl)fluorene residue; $R_2$ represents a 9,9-bis(4-aminophenyl)fluorene residue; $R_3$ and $R_4$ each represent a 1,2,4,5-benzenetetracarboxylic dianhydride residue; and m=3.6 and n=0.4 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % did not gel even after storage for one month. The lowest melt viscosity of the powdery terminally modified imide oligomer was 154 Pa·s (325° C.) before curing. The film-shaped cured product (thickness: 111 μm) obtained by heating the powdery terminally modified imide oligomer at 370° C. by using a hot press for 1 hour had a Tg of 371° C. (DSC) and a 5% weight-loss temperature of 538° C., as determined by TGA. Analysis of the mechanical properties by tensile tests showed that had a modulus of 2.97 GPa, a breaking strength of 119 MPa, and a breaking elongation of 13%.

A plain-weave fabric "BESFIGHT IM-600 6K" (made of carbon fiber; fiber basis weight: 195 g/m) of 30 cm×30 cm in size (produced by TOHO TENAX Co., Ltd.) previously desized with acetone was impregnated with the remaining reaction solution (solid matter concentration: 35 wt %) after cooling. The fabric was dried at 100° C. in a drier for 10 minutes to give an imide prepreg. The resin content of the prepreg obtained was 38% and the residual volatile material content was 17%.

Comparative Example 12

1.8022 g (9.0 mmol) of 4,4'-diaminodiphenylether, 0.3484 g (1.0 mmol) of 9,9-bis(4-aminophenyl)fluorene and 9.6 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride was added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated during the imidation reaction.

After cooling, the reaction solution was poured into 900 mL of ion-exchange water, and the precipitated powder was collected by filtration. The powder was washed with 60 mL of methanol for 30 minutes and filtered, and the powder obtained by filtration was dried under reduced pressure at 130° C. for one day, to give a product. The terminally modified imide oligomer thus obtained has a structure of the following General Formula (3), in which $R_1$ represents a 4,4'-diaminodiphenylether residue or a 9,9-bis(4-aminophenyl)fluorene residue; $R_2$ represents a 9,9-bis(4-aminophenyl)fluorene residue; and m=3.6 and n=0.4 on average.

The powdery uncured product of terminally modified imide oligomer thus obtained was insoluble in NMP solvent at room temperature. The powdery terminally modified imide oligomer did not show melt fluidity even at 300° C. or higher and did not give a favorable shaped product (cured film-shaped product).

Example 12

2.0709 g (7.5 mmol) of 2-phenyl-4,4'-diaminodiphenylether, 0.8711 g (2.5 mmol) of 9,9-bis(4-aminophenyl)fluorene and 10 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride and 1.2 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.9929 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, the reaction solution was poured into 900 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue or a 9,9-bis(4-aminophenyl)fluorene residue; $R_2$ represents a 9,9-bis(4-aminophenyl)fluorene residue; $R_3$ and $R_4$ each represent a 1,2,4,5-benzenetetracarboxylic dianhydride residue; and m=3 and n=1 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % did not gel even after storage for one month. The lowest melt viscosity of the powdery terminally modified imide oligomer was 1323 Pa·s (351° C.) before curing. The film-shaped cured product (thickness: 175 μm) obtained by heating the powdery terminally modified imide oligomer at 370 to 420° C. by using a hot press for 1 hour had a Tg of 396° C. (DSC) and a 5% weight-loss temperature of 544° C., as determined by TGA. Analysis of the mechanical properties by tensile tests showed that had a modulus of 2.82 GPa, a breaking strength of 101 MPa, and a breaking elongation of 11%.

Comparative Example 13

1.5018 g (7.5 mmol) of 4,4'-diaminodiphenylether, 0.8711 g (2.5 mmol) of 9,9-bis(4-aminophenyl)fluorene and 10 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride was added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated during the imidation reaction.

After cooling, the reaction solution was poured into 900 mL of ion-exchange water, and the precipitated powder was collected by filtration. The powder was washed with 60 mL of methanol for 30 minutes and filtered, and the powder obtained by filtration was dried under reduced pressure at 130° C. for one day, to give a product. The terminally modified imide oligomer thus obtained has a structure of the following General Formula (3), in which $R_1$ represents a 4,4'-diaminodiphenylether residue or a 9,9-bis(4-aminophenyl)fluorene residue; $R_2$ represents a 9,9-bis(4-aminophenyl)fluorene residue; and m=3 and n=1 on average.

The powdery uncured product of terminally modified imide oligomer thus obtained was insoluble in NMP solvent at room temperature. The powdery terminally modified imide oligomer did not show melt fluidity even at 300° C. or higher and did not give a favorable shaped product (cured film-shaped product).

Comparative Example 14

3.4844 g (10 mmol) of 9,9-bis(4-aminophenyl)fluorene and 10 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride and 2.3 mL of N-methyl-2-pyrrolidone were added thereto; and the mixture was allowed to react in polymerization reaction under nitrogen stream at room temperature for 2.5 hours, at 60° C. for 1.5 hours and additionally at room temperature for 1 hour, to give an amide acid oligomer. 0.993 g (4 mmol) of 4-(2-phenylethynyl)phthalic anhydride was added to the reaction solution; and the mixture was allowed to react for terminal modification under nitrogen stream at room temperature for 12 hours and then stirred at 195° C. for 5 hours for imidation. The imide oligomer precipitated during the imidation reaction.

After cooling, the reaction solution was poured into 900 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (3), in which $R_1$ and $R_2$ represents a 9,9-bis(4-aminophenyl)fluorene residue; and m=0 and n=4 on average.

The powdery uncured product of terminally modified imide oligomer thus obtained was insoluble in NMP solvent at room temperature. The powdery terminally modified imide oligomer did not show melt fluidity even at 300° C. or higher and did not give a favorable shaped product (cured film-shaped product).

Example 13

4.9703 g (18.0 mmol) of 2-phenyl-4,4'-diaminodiphenylether, 0.2163 g (2.0 mmol) of 1,3-diaminobenzene and 20 mL of N-methyl-2-pyrrolidone were placed and dissolved in a 100 mL three-necked flask equipped with a thermometer, a stirring bar, and a nitrogen-supplying tube; 3.4899 g (16 mmol) of 1,2,4,5-benzenetetracarboxylic dianhydride and 1 mL of N-methyl-2-pyrrolidone were added thereto; and the mixture was allowed to react in polymerization reaction under nitrogen stream at room temperature for 2.5 hours, to give an amide acid oligomer. 1.9858 g (8 mmol) of (2-phenylethynyl)phthalic anhydride was added to the reaction solution; and the mixture was allowed to react for terminal modification under nitrogen stream at room temperature for 12 hours and then stirred at 195° C. for 5 hours for imidation.

After cooling, the reaction solution was poured into 900 mL of ion-exchange water, and the precipitated powder was collected by filtration. The powder was washed with 80 mL of methanol for 30 minutes and filtered, and the powder obtained by filtration was dried under reduced pressure at 130° C. for one day, to give a product. The terminally modified imide oligomer thus obtained has a structure of the following General Formula (1), in which $R_1$ represents a 2-phenyl-4,4'-diaminodiphenylether residue or a 1,3- diaminobenzene residue; $R_2$ represents a 1,3-diaminobenzene residue; $R_3$ and $R_4$ each represent a 1,2,4,5-benzenetetradianhydride carboxylate residue; and m=3.6 and n=0.4 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % did not gel even after storage for one month. The lowest melt viscosity of the powdery terminally modified imide oligomer was 199 Pa·s (343° C.) before curing. The film-shaped cured product (thickness; 111 μm) obtained by heating the powdery terminally modified imide oligomer at 370° C. by using a hot press for 1 hour had a Tg of 365° C. (DSC) and a 5% weight-loss temperature of 541° C., as determined by TGA. Analysis of the mechanical properties by tensile tests showed that had a modulus of 2.84 GPa, a breaking strength of 116 MPa, and a breaking elongation of 15%.

Example 14

4.4181 g (16 mmol) of 2-phenyl-4,4'-diaminodiphenylether and 20 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride and 3 mL of N-methyl-2-pyrrolidone were added thereto; and the mixture was allowed to react in polymerization reaction under nitrogen stream at room temperature for 2.5 hours, to give an amide acid oligomer. 3.9717 g (16 mmol) of 4-(2-phenylethynyl)phthalic anhydride was added to the reaction solution; the mixture was allowed to react for terminal modification under nitrogen stream at room temperature for 18 hours and then stirred at 195° C. for 5 hours for imidation.

After cooling, the reaction solution was poured into 900 mL of ion-exchange water, and the precipitated powder was collected by filtration. The powder obtained by filtration was dried at 100° C. under reduced pressure for one day, to give a product. The terminally modified imide oligomer thus obtained has a structure of the following General Formula (1), in which $R_1$ represents a 2-phenyl-4,4'-diaminodiphenylether residue; $R_3$ represents a 1,2,4,5-benzenetetracarboxylic dianhydride residue; and m=1 and n=0 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % did not gel even after storage for one month. The lowest melt viscosity of the powdery terminally modified imide oligomer was 0.8 Pa·s (325° C.) before curing. The film-shaped cured product (thickness: 80 μm) obtained by heating the powdery terminally modified imide oligomer at 370° C. by using a hot press for 1 hour had a Tg of 367° C. (DSC) and a 5% weight-loss temperature of 528° C., as determined by TGA. Analysis of the mechanical properties by tensile tests showed that had a modulus of 3.08 GPa, a breaking strength of 121 MPa, and a breaking elongation of 12%.

Example 15

3.3136 g (12 mmol) of 2-phenyl-4,4'-diaminodiphenylether and 10 mL of N-methyl-2-pyrrolidone were placed and dissolved in a 100 mL three-necked flask equipped with a thermometer, a stirring bar, and a nitrogen-supplying tube; 1.7450 g (8 mmol) of 1,2,4,5-benzenetetracarboxylic dianhydride and 3 mL of N-methyl-2-pyrrolidone were added thereto; and the mixture was allowed to react in polymerization reaction under nitrogen stream at room temperature for 2.5 hours, to give an amide acid oligomer. 1.9858 g (8 mmol) of 4-(2-phenylethynyl)phthalic anhydride was added to the reaction solution; and the mixture was allowed to react for terminal modification under nitrogen stream at room temperature for 18 hours and then stirred at 195° C. for 5 hours for imidation.

After cooling, the reaction solution was poured into 900 mL of ion-exchange water, and the precipitated powder was collected by filtration. The powder obtained by filtration was dried at 100° C. under reduced pressure for one day, to give a product. The terminally modified imide oligomer thus obtained has a structure of the following General Formula (1), in which $R_1$ represents a 2-phenyl-4,4'-diaminodiphenylether residue; $R_3$ represents a 1,2,4,5-benzenetetracarboxylic dianhydride residue; and m=1 and n=0 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % did not gel even after storage for one month. The lowest melt viscosity of the powdery terminally modified imide oligomer was 30 Pa·s (338° C.) before curing. The film-shaped cured product (thickness; 90 μm) obtained by heating the powdery terminally modified imide oligomer at 370° C. by using a hot press for 1 hour had a Tg of 355° C. (DSC) and a 5% weight-loss temperature of 529° C., as determined by TGA. Analysis of the mechanical properties by tensile tests showed that had a modulus of 2.93 GPa, a breaking strength of 120 MPa, and a breaking elongation of 12%.

Example 16

3.0374 g (11 mmol) of 2-phenyl-4,4'-diaminodiphenylether and 10 mL of N-methyl-2-pyrrolidone were placed and dissolved in a 100 mL three-necked flask equipped with a thermometer, a stirring bar, and a nitrogen-supplying tube; 2.1812 g (10 mmol) of 1,2,4,5-benzenetetracarboxylic dianhydride and 3 mL of N-methyl-2-pyrrolidone were added thereto; and the mixture was allowed to react in polymerization reaction under nitrogen stream at room temperature for 2.5 hours, to give an amide acid oligomer. 0.4964 g (2 mmol) of 4-(2-phenylethynyl)phthalic anhydride was added to the reaction solution; and the mixture was allowed to react for terminal modification under nitrogen stream at room temperature for 18 hours and then stirred at 195° C. for 5 hours for imidation.

After cooling, the reaction solution was poured into 900 mL of ion-exchange water, and the precipitated powder was collected by filtration. The powder obtained by filtration was dried at 100° C. under reduced pressure for one day, to give a product. The terminally modified imide oligomer thus obtained has a structure of the following General Formula (1), in which $R_1$ represents a 2-phenyl-4,4'-diaminodiphenylether residue; $R_3$ represents a 1,2,4,5-benzenetetracarboxylic dianhydride residue; and m=10 and n=0 on average.

The powdery uncured product of terminally modified imide oligomer thus obtained was soluble in NMP solvent in an amount of 30 wt % or more at room temperature. The NMP solution (varnish) containing the powdery terminally modified imide oligomer dissolved at 30 wt % gelled in several days when left still at room temperature, but returned to liquid state when heated once again to 80° C. The solution gelled again in several days when left still at room temperature. The lowest melt viscosity of the powdery terminally modified imide oligomer was 11100 Pa·s (330° C.) before curing. The film-shaped cured product (thickness: 175 μm) obtained by heating the powdery terminally modified imide oligomer at 370° C. by using a hot press for 1 hour had a Tg of 341° C. (DSC) and a 5% weight-loss temperature of 542° C., as determined by TGA. Analysis of the mechanical properties by tensile tests showed that had a modulus of 2.82 GPa, a breaking strength of 110 MPa, and a breaking elongation of 15%.

Example 17

3.3136 g (12 mmol) of 2-phenyl-4,4'-diaminodiphenylether and 12 mL of N-methyl-2-pyrrolidone 12 mL were placed and dissolved in a 100 mL three-necked flask equipped with a thermometer, a stirring bar, and a nitrogen-supplying tube; 1.8846 g (8.64 mmol) of 1,2,4,5-benzenetetracarboxylic dianhydride, 0.2824 g (0.96 mmol) of 3,3',4,4'-biphenyltetracarboxylic dianhydride and 3 mL of N-methyl-2-pyrrolidone were added thereto; and the mixture was allowed to react in polymerization reaction under a nitrogen stream at room temperature for 2.5 hours, to give an amide acid oligomer. 1.1915 g (4.8 mmol) of 4-(2-phenylethynyl)phthalic anhydride was added to the reaction solution; and the mixture was allowed to react for terminal modification under nitrogen stream at room temperature for 18 hours and then stirred at 195° C. for 5 hours for imidation.

After cooling, the reaction solution was poured into 900 mL of ion-exchange water, and the precipitated powder was collected by filtration. The powder obtained by filtration was dried at 150° C. under reduced pressure for one day, to give a product. The terminally modified imide oligomer thus obtained has a structure of the following General Formula (1), in which $R_1$ and $R_2$ each represent a 2-phenyl-4,4'-diaminodiphenylether residue; $R_3$ represents a 1,2,4,5-benzenetetracarboxylic dianhydride residue; $R_4$ represents a 3,3',4,4'-biphenyltetracarboxylic dianhydride residue; and m=3.6 and n=0.4 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % gelled in several days when left still at room temperature, but returned to liquid state when heated once again to 80° C. The solution gelled again in several days when left still at room temperature. The lowest melt viscosity of the powdery terminally modified imide oligomer was 449 Pa·s (° C.) before curing. The film-shaped cured product (thickness: 85 μm) obtained by heating the powdery terminally modified imide oligomer at 370° C. by using a hot press for 1 hour had a Tg of 350° C. (DSC) and a 5% weight-loss temperature of 539° C., as determined by TGA. Analysis of the mechanical properties by tensile tests showed that had a modulus of 3.15 GPa, a breaking strength of 127 MPa, and a breaking elongation of 19%.

Example 18

3.3136 g (12 mmol) of 2-phenyl-4,4'-diaminodiphenylether and 12 mL of N-methyl-2-pyrrolidone were placed and dissolved in a 100 mL three-necked flask equipped with a thermometer, a stirring bar, and a nitrogen-supplying tube; 1.8846 g (8.64 mmol) of 1,2,4,5-benzene tetracarboxylic dianhydride, 0.2978 g (0.96 mmol) of bis(3,4-carboxyphenyl)ether dianhydride and 3 mL of N-methyl-2-pyrrolidone 3 mL were added thereto; and the mixture was allowed to react in polymerization reaction under nitrogen stream at room temperature for 2.5 hours, to give an amide acid oligomer. 1.1915 g (4.8 mmol) of 4-(2-phenylethynyl)phthalic anhydride was added to the reaction solution; and the mixture was allowed to react for terminal modification under nitrogen stream at room temperature for 18 hours and then stirred at 195° C. for 5 hours for imidation.

After cooling, the reaction solution was poured into 900 mL of ion-exchange water, and the precipitated powder was collected by filtration. The powder obtained by filtration was dried at 150° C. under reduced pressure for one day, to give a product. The terminally modified imide oligomer thus obtained has a structure of the following General Formula (1), in which $R_1$ and $R_2$ each represent 2-phenyl-4,4'-diaminodiphenylether residue; $R_3$ represents a 1,2,4,5-benzenetetracarboxylic dianhydride residue; R4 represents a bis(3,4-carboxyphenyl)ether dianhydride residue; and m=3.6 and n=0.4 on average.

The powdery uncured product of terminally modified imide oligomer thus obtained was soluble in NMP solvent in an amount of 30 wt % or more at room temperature. The NMP solution (varnish) containing the terminally modified imide oligomer dissolved at 30 wt % gelled in several days when left still at room temperature, but returned to liquid state when heated once again to 80° C. The solution gelled again in several days when left still at room temperature. The lowest melt viscosity of the powdery terminally modified imide oligomer was 159 Pa·sec before curing. The film-shaped cured product (thickness; 85 μm) obtained by heating the powdery terminally modified imide oligomer at 370° C. by using a hot press for 1 hour had a Tg of 344° C. (DSC) and a 5% weight-loss temperature of 540° C., as determined by TGA. Analysis of the mechanical properties by tensile tests showed that had a modulus of 2.98 GPa, a breaking strength of 135 MPa, and a breaking elongation of 17%.

Example 19

A polyimide film was formed as release film on a stainless steel plate of 30 cm×30 cm in size, and 12 layers of the prepregs prepared in Example 11 were laminated thereon. In addition, the pile of the polyimide films and the stainless steel plate was heated, in a hot press under vacuum, at a heating speed of 5° C./min to 260° C., consistently at 260° C. for 2 hours, at a heating speed of 3° C./min to 370° C. under a load of 1.3 MPa, and additionally at 370° C. under pressure for 1 hour. A favorable laminate without large voids, as determined from appearance, ultrasonic flaw test and cross-sectional observation, was obtained. The glass transition temperature of the laminate obtained was 358° C.; the fiber volume rate (vf) was 0.60; and the resin content was 33 wt %.

Industrial Applicability

The present invention provides a new terminally modified imide oligomer superior in solubility in organic solvent and capable of forming a film, solution storage stability, and moldability such as low melt viscosity, which gives a cured product superior in heat resistance and mechanical properties such as tensile modulus, tensile breaking strength, and tensile breaking elongation, and also a varnish containing the same and a cured product thereof, which are materials usable in a wide range of applications demanding favorable moldability and high heat resistance, for example as parts for aircrafts and devices for the airspace industry.

The invention claimed is:

1. A terminally modified imide oligomer of General Formula (1),

General Formula (1)

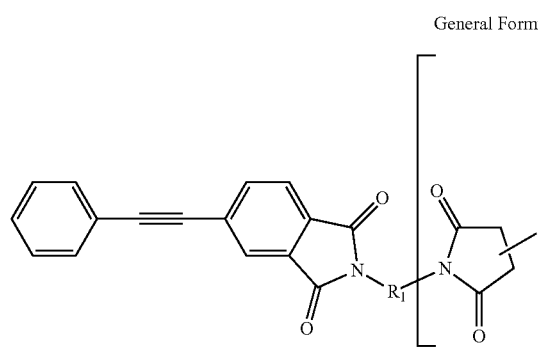

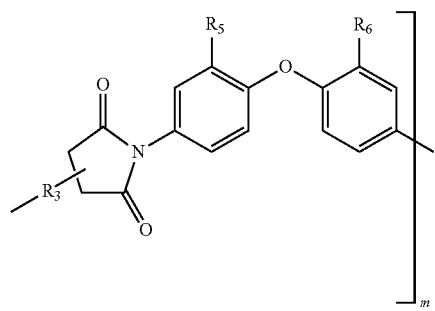

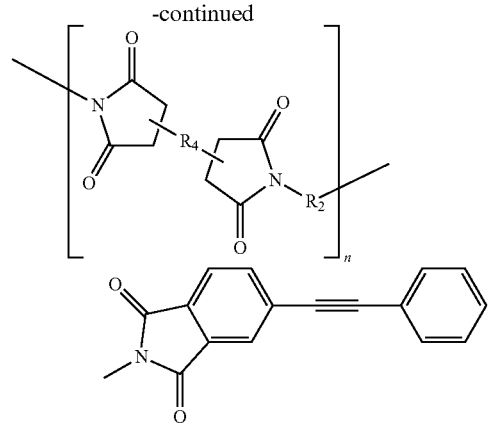

wherein $R_1$ and $R_2$ each represent bivalent aromatic diamine residue;
$R_3$ and $R_4$ each represent tetravalent aromatic tetracarboxylic acid residue;
$R_5$ and $R_6$ are each independently selected from a hydrogen atom and a phenyl group, wherein at least one of $R_5$ or $R_6$ is a phenyl group;
m and n satisfy the following relations: $m \geq 1$, $n \geq 0$, $1 \leq m+n \leq 20$ and $0.05 \leq m/(m+n) \leq 1$;
the repeating units may be arranged in blocks or arranged randomly; and
wherein the terminally modified imide oligomer is soluble in N-methyl-2-pyrrolidone at a solid matter concentration of at least 30 wt % at room temperature.

2. The terminally modified imide oligomer according to claim 1, represented by the following General Formula (1-2), wherein $R_3$ and $R_4$ are each 1,2,4,5-benzenetetracarboxylic acid, General Formula (1-2)

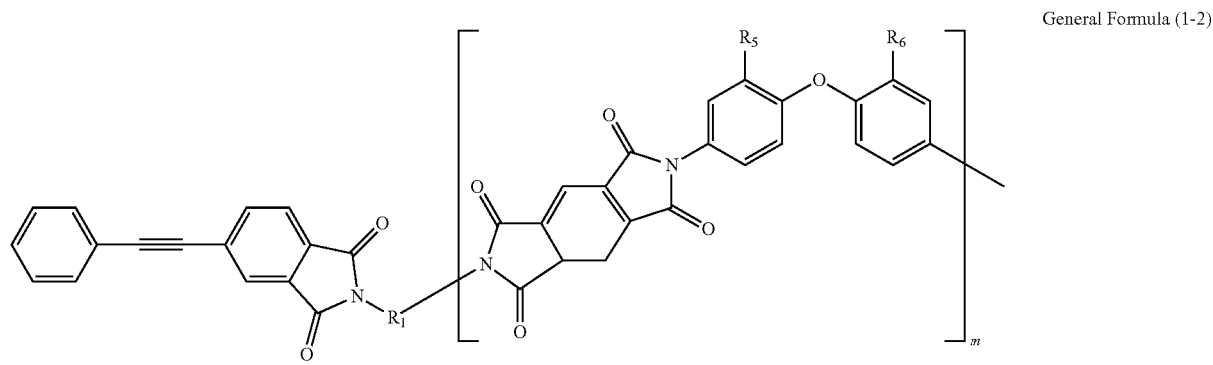

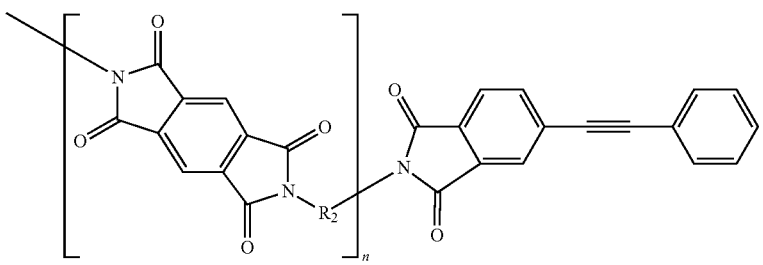

wherein R$_1$ and R$_2$ each represent bivalent aromatic diamine residue;

R$_5$ and R$_6$ each represent hydrogen atom or a phenyl group, wherein at least one of R$_5$ and R$_6$ is a phenyl group;

m and n satisfy the following relations: m≥1, n≥0, 1≤m+n≤20 and 0.05≤m/(m+n)≤1; and the repeating units may be arranged in blocks or arranged randomly.

3. The terminally modified imide oligomer according to claim 1, represented by the following General Formula (1-3), wherein R$_3$ and R$_4$ are each 3,3',4,4'-biphenyltetracarboxylic acid, General Formula (1-3)

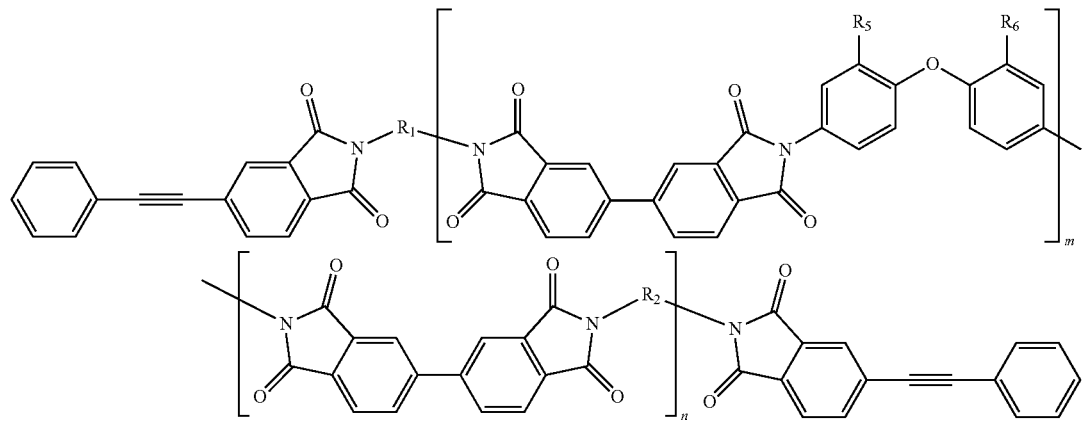

wherein R$_1$ and R$_2$ each represent bivalent aromatic diamine residue;

R$_5$ and R$_6$ each represent hydrogen atom or a phenyl group, wherein at least one of R$_5$ and R$_6$ is a phenyl group;

m and n satisfy the following relations: m≥1, n ≥0, 1≤m+n≤20 and 0.05≤m/(m+n)≤1; and the repeating units may be arranged in blocks or arranged randomly.

4. The terminally modified imide oligomer according to claim 1, wherein the tetravalent aromatic tetracarboxylic acid residue is a combination of at least two compounds selected from the group consisting of 1,2,4,5-benzenetetracarboxylic acid, 3,3',4,4-biphenyltetracarboxylic acid and bis(3,4-carboxyphenyl)ether.

5. The terminally modified imide oligomer according to claim 1, wherein the bivalent aromatic diamine residue represented by R$_1$ and R$_2$ is a bivalent residue derived from at least one aromatic diamine compound selected from the group consisting of 9,9-bis(4-aminophenyl)fluorene, 9,9-bis(4-(4-aminophenoxy)phenyl)fluorine and 1,3-diaminobenzene.

6. A varnish, comprising the terminally modified imide oligomer according to claim 1 and an organic solvent, wherein the terminally modified imide oligomer is dissolved in the organic solvent.

7. A cured product, comprising the varnish according to claim 6, wherein the varnish is cured under heat.

8. The cured product according to claim 7, wherein the cured product has a glass transition temperature (Tg) of 300° C. or higher.

9. A cured product, comprising the terminally modified imide oligomer according to claim 1, wherein the terminally modified imide oligomer is cured under heat.

10. The cured product according to claim 9, wherein the cured product has a glass transition temperature (Tg) of 300° C. or higher.

11. A film comprising the cured product according to claim 9, wherein the film has a tensile breaking elongation of 10% or more.

12. An imide prepreg, comprising a fiber that is impregnated with the varnish according to claim 6, wherein the fiber that is impregnated with the varnish is dried.

13. The imide prepreg according to claim 12, wherein the resin content of the imide prepreg is 30 to 50 wt %.

14. A fiber-reinforced laminate, comprising a plurality of the imide prepregs according to claim 12, wherein the plurality of the imide prepregs is laminated and then heated.

15. The fiber-reinforced laminate according to claim 14, wherein the fiber-reinforced laminate has a glass transition temperature (Tg) of 300° C. or higher.

16. A fiber-reinforced laminate, comprising fiber fabrics that are impregnated with a powder of the terminally modified imide oligomer according to claim 1, wherein the fiber fabrics that are impregnated with the powder of the terminally modified imide oligomer is laminated and then cured under heat.

17. The fiber-reinforced laminate according to claim 16, wherein the fiber-reinforced laminate has a glass transition temperature (Tg) of 300° C. or higher.

18. A film comprising the cured product according to claim 7, wherein the tensile breaking elongation of the film is 10% or more.

19. A fiber-reinforced laminate, comprising a plurality of the imide prepregs according to claim 13, wherein the plurality of the imide prepregs are laminated and then heated.

* * * * *